United States Patent
Smith et al.

(10) Patent No.: US 11,878,094 B2
(45) Date of Patent: Jan. 23, 2024

(54) HUMIDIFIER TUB FOR CPAP DEVICE

(71) Applicant: ResMed Pty Ltd, Bella Vista (AU)

(72) Inventors: Ian Malcolm Smith, Sydney (AU); William Bonilla, Melbourne (AU); Richard Llewelyn Jones, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 18/352,453

(22) Filed: Jul. 14, 2023

(65) Prior Publication Data

US 2023/0355913 A1  Nov. 9, 2023

Related U.S. Application Data

(63) Continuation of application No. 16/855,180, filed on Apr. 22, 2020, now Pat. No. 11,738,166, which is a
(Continued)

(51) Int. Cl.
*A61M 16/00* (2006.01)
*A61M 16/16* (2006.01)
(Continued)

(52) U.S. Cl.
CPC ........ *A61M 16/16* (2013.01); *A61M 16/0066* (2013.01); *A61M 16/0666* (2013.01);
(Continued)

(58) Field of Classification Search
CPC ............... A61M 16/16; A61M 16/109; A61M 16/0066; A61M 16/0666; A61M 16/0875; A61M 2206/14; A61M 2206/16
See application file for complete search history.

(56) References Cited

U.S. PATENT DOCUMENTS

| 3,804,280 A | 4/1974 | Van Amerongen et al. |
| 3,806,102 A | 4/1974 | Valenta et al. |
| (Continued) | | |

FOREIGN PATENT DOCUMENTS

| JP | 2004-057278 | 2/2004 |
| WO | 2002/13898 A2 | 2/2002 |
| (Continued) | | |

OTHER PUBLICATIONS

Corrected Notice of Allowability dated May 11, 2017 issued in U.S. Appl. No. 11/988,718 (6 pages).
(Continued)

*Primary Examiner* — Steven O Douglas
(74) *Attorney, Agent, or Firm* — Nixon & Vanderhye P.C.

(57) ABSTRACT

A humidifier tub includes a first side having an air inlet opening configured to receive the pressurized flow of respiratory gas. A second side opposes the first side. An air outlet opening is configured to discharge the pressurized flow of respiratory gas with added humidity. An inlet passage extends from the air inlet opening toward the second side so that the pressurized flow of respiratory gas travels through the inlet passage in a first direction. A guidance structure is located between the first and second sides and positioned so that a traveling direction of the pressurized flow of respiratory gas changes from the first direction to a second direction upon the pressurized flow of respiratory gas engaging the guidance structure. The guidance structure extends downward from a lid. In addition, the first direction is a lateral direction and the second direction is a downward direction.

27 Claims, 24 Drawing Sheets

Related U.S. Application Data continuation of application No. 15/332,037, filed on Oct. 24, 2016, now Pat. No. 10,661,043, which is a continuation of application No. 11/988,718, filed as application No. PCT/AU2006/001171 on Aug. 15, 2006, now Pat. No. 9,707,370.

(60) Provisional application No. 60/707,949, filed on Aug. 15, 2005.

(51) Int. Cl.
  *A61M 16/10* (2006.01)
  *A61M 16/06* (2006.01)
  *A61M 16/08* (2006.01)

(52) U.S. Cl.
  CPC ...... *A61M 16/0875* (2013.01); *A61M 16/109* (2014.02); *A61M 2206/14* (2013.01); *A61M 2206/16* (2013.01)

(56) References Cited

U.S. PATENT DOCUMENTS

| | | | |
|---|---|---|---|
| 4,152,379 A | 5/1979 | Suhr | |
| 4,203,027 A | 5/1980 | O'Hare et al. | |
| 4,621,632 A | 11/1986 | Bartels et al. | |
| 4,921,642 A | 5/1990 | LaTorraca | |
| 4,943,704 A | 7/1990 | Rabenau et al. | |
| 4,944,310 A | 7/1990 | Sullivan | |
| 5,794,986 A | 8/1998 | Gansel et al. | |
| 5,826,575 A | 10/1998 | Lall | |
| 5,943,473 A | 8/1999 | Levine | |
| 6,349,722 B1 | 2/2002 | Gradon | |
| 6,398,197 B1 | 6/2002 | Dickinson et al. | |
| 6,718,973 B2 | 4/2004 | Koch | |
| 6,827,340 B2 | 12/2004 | Austin | |
| 6,918,389 B2 | 7/2005 | Seakins | |
| 7,111,624 B2 | 9/2006 | Thudor et al. | |
| 7,413,173 B2 | 8/2008 | DiMatteo et al. | |
| 7,616,871 B2 | 11/2009 | Kramer | |
| 9,707,370 B2 | 7/2017 | Smith et al. | |
| 10,661,043 B2 | 5/2020 | Smith et al. | |
| 2003/0066526 A1 | 4/2003 | Thudor et al. | |
| 2005/0087071 A1 | 4/2005 | Petz et al. | |
| 2010/0154796 A1 | 6/2010 | Smith et al. | |
| 2017/0035984 A1 | 2/2017 | Smith et al. | |
| 2020/0246576 A1 | 8/2020 | Smith et al. | |

FOREIGN PATENT DOCUMENTS

| | | |
|---|---|---|
| WO | 02/066107 | 8/2002 |
| WO | 2003/099367 | 12/2003 |
| WO | 2004/108198 | 12/2004 |
| WO | 2004/112873 | 12/2004 |
| WO | 2005/103339 | 11/2005 |
| WO | 2006/012877 | 2/2006 |

OTHER PUBLICATIONS

International Search Report for PCT/AU2006/001171 dated Oct. 30, 2006.

U.S. Appl. No. 60/707,951, filed Aug. 15, 2005 (p. 6 of the specification).

Extended Search Report issued in related European Appln. No. 06774816 (dated May 24, 2011).

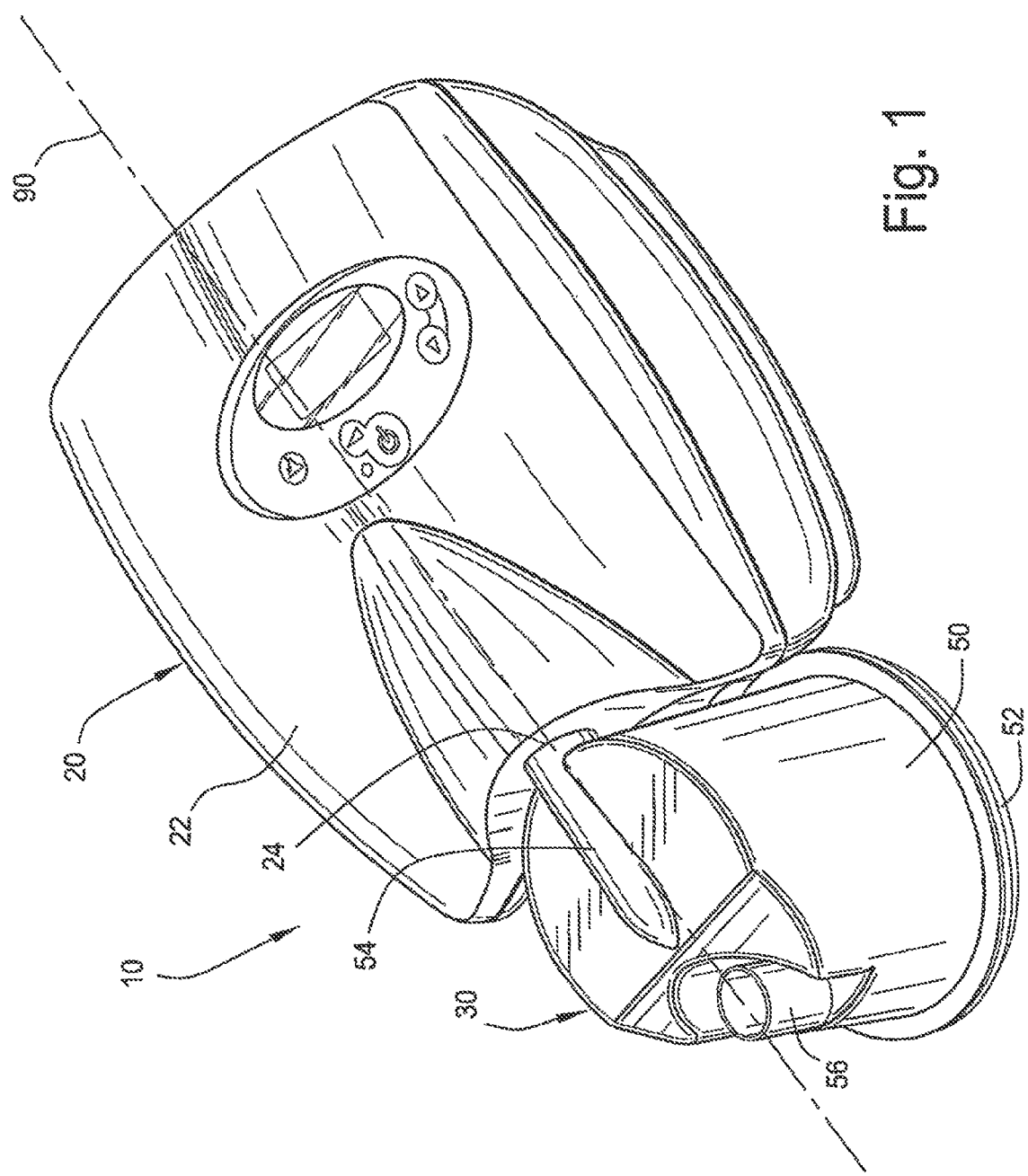

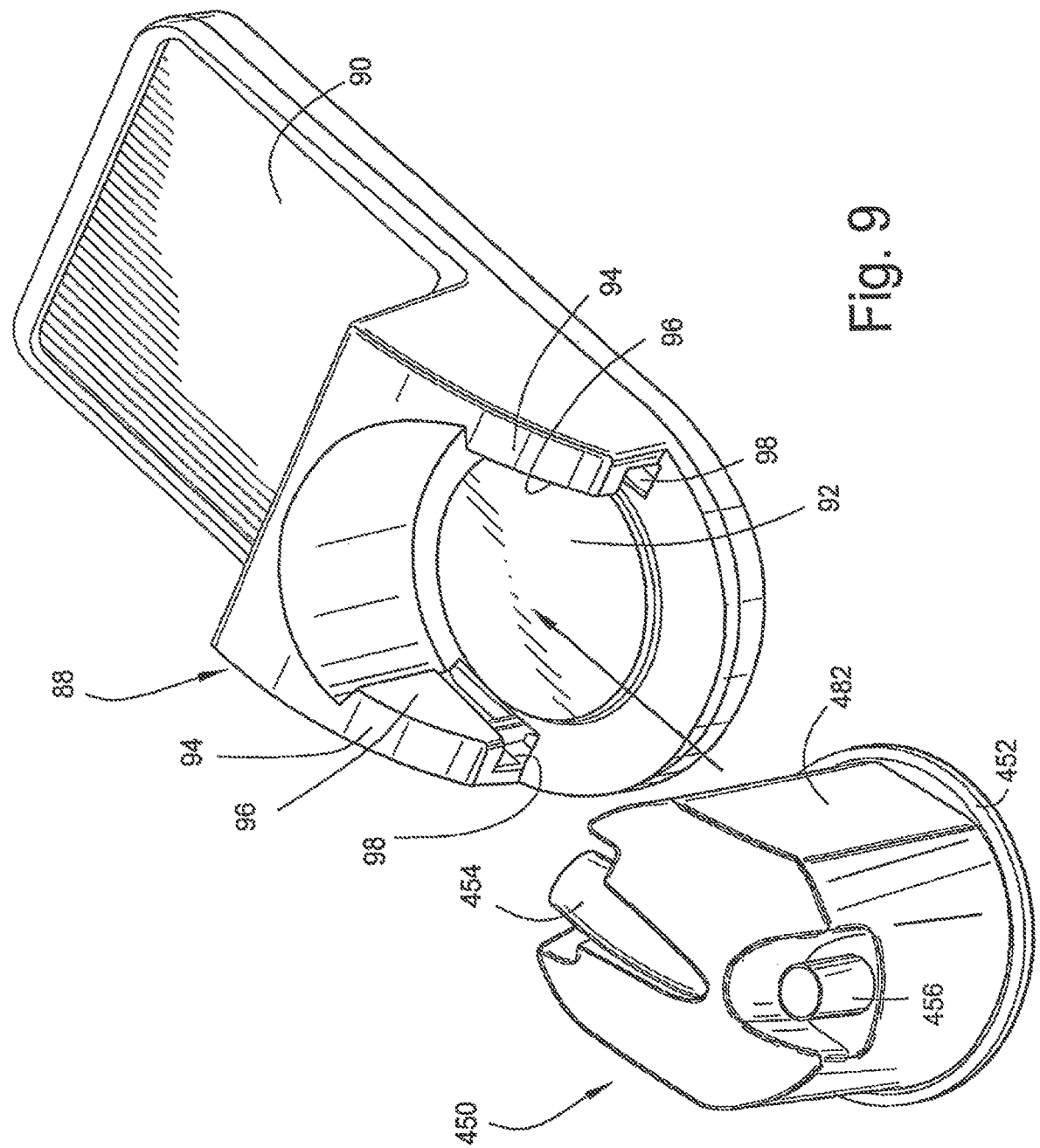

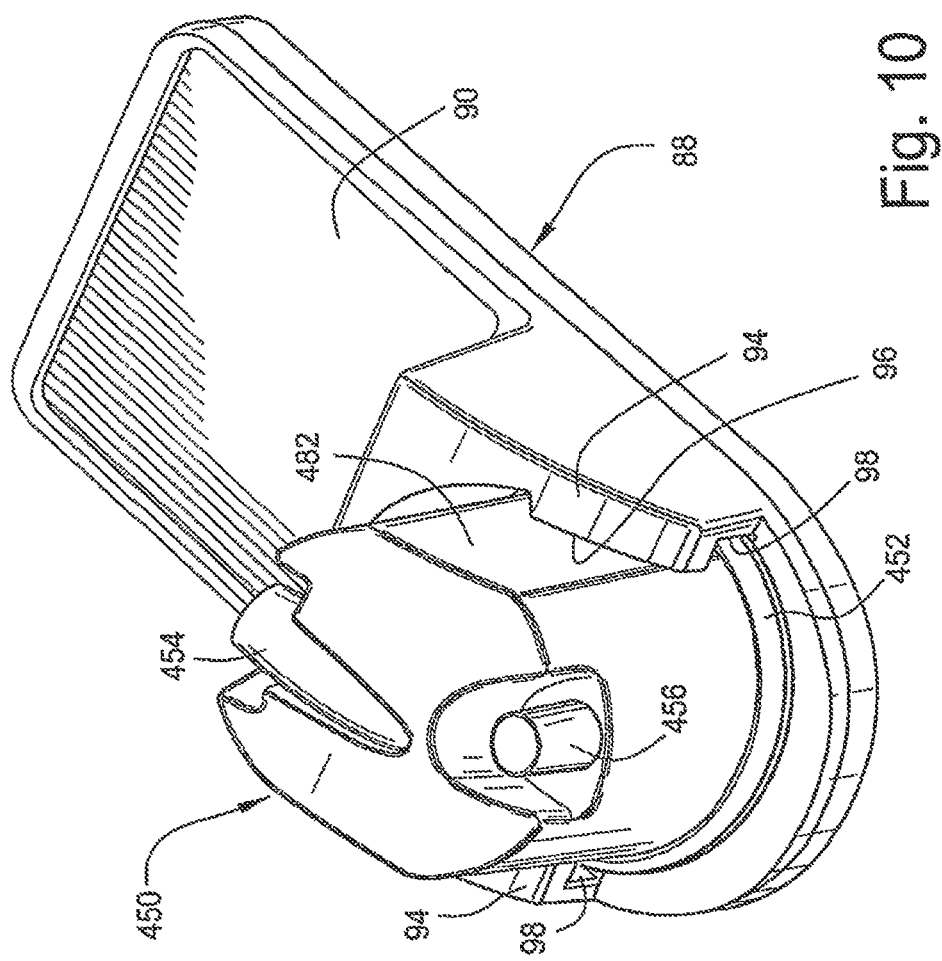

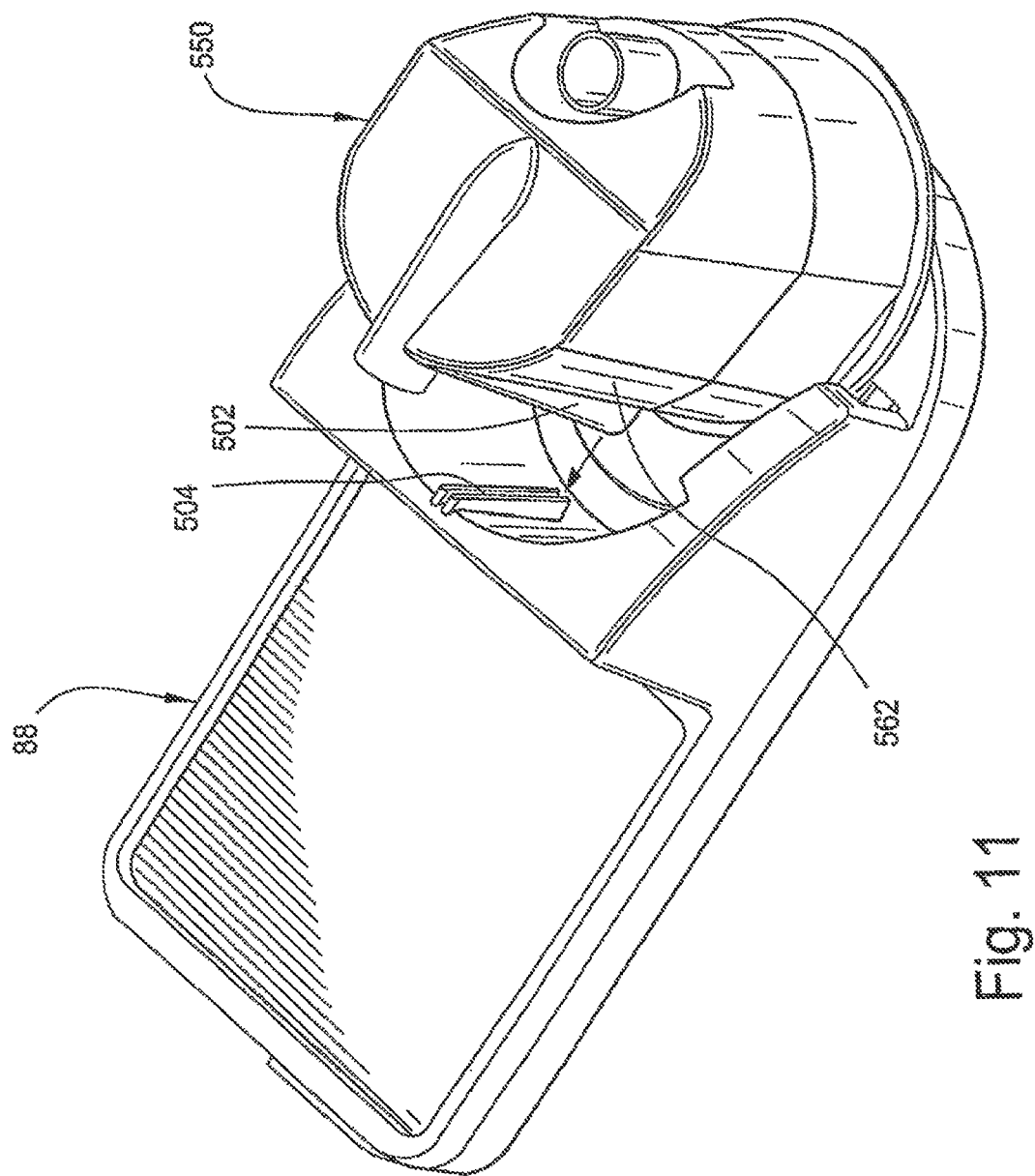

HUMIDIFIER TUB FOR CPAP DEVICE

CROSS-REFERENCE TO PRIORITY APPLICATION

This application is a continuation of U.S. application Ser. No. 16/855,180, filed Apr. 22, 2020, now allowed, which is a continuation of U.S. application Ser. No. 15/332,037, now U.S. Pat. No. 10,661,043, filed Oct. 24, 2016, which is a continuation of U.S. application Ser. No. 11/988,718, now U.S. Pat. No. 9,707,370, filed Jan. 14, 2008, which is the U.S. national phase of International Application No. PCT/AU2006/001171 filed 15 Aug. 2006 which designated the U.S. and claims priority to U.S. Provisional Application No. 60/707,949 filed 15 Aug. 2005, the entire contents of each of which are hereby incorporated by reference.

FIELD OF THE INVENTION

The present invention relates to an improved humidifier tub that is adapted to form part of a Continuous Positive Airway Pressure (CPAP) flow generator with a humidification system used to treat sleep disordered breathing (SDB) conditions such as Obstructive Sleep Apnea (OSA).

BACKGROUND OF THE INVENTION

Colin Sullivan was the first to invent the use of nasal Continuous Positive Airway Pressure (CPAP) to treat Obstructive Sleep Apnea (OSA), e.g., see U.S. Pat. No. 4,944,310. The treatment generally provides a supply of air or breathable gas from a blower to a patient via an air delivery conduit and a patient interface, such as a full-face or nasal mask or nasal prongs. The air or breathable gas is commonly delivered at a pressure of 4cmH$_2$O to 20cmH$_2$O and acts as a splint to hold the airway open during sleep.

Humidifiers are commonly used with CPAP flow generators to prevent a patient's airways from drying out. The humidified air is generally heated allowing the air to carry more moisture and to provide additional comfort for the patient. A humidifier normally comprises a water tub, a heating element, an air inlet able to receive air from the CPAP flow generator, and an outlet adapted to connect to a delivery conduit to deliver the humidified air through the patient interface to the patient. A humidifier may be integrated or adapted for coupling with a CPAP flow generator. The humidifier is often detachable to allow the water tub to be removed for filling with water.

Humidifier tubs may be washable or disposable. Disposable humidifier tubs are well known in the prior art, e.g., see U.S. Pat. No. 4,203,027 (O'Hare et al.) published 13 May 1980 and U.S. Pat. No. 6,398,197 (Dickinson et al.) published 4 Jun. 2002.

As humidifier systems and tubs become smaller, the surface area of water exposed to the delivered air also inherently becomes smaller, creating problems in maintaining a sufficient moisture pickup by the air flow passing through the tub. The use of baffles between the air inlet and air outlet has been used to encourage the incoming air to flow around the surface of the container and down to the water surface prior to exiting from the air outlet. This suffers from the disadvantage that the air flow suffers a significant pressure drop, thus requiring the flow generator motor to run faster to overcome this drop in pressure and consequently producing more noise.

Another problem with current humidifier tubs is that if the tub is filled above the indicated level, in particular while the tub is connected to the flow generator, the water may flow back into the flow generator.

A further problem with prior art humidifier tubs, especially round tubs, was that users, particularly those users with limited dexterity or poor eyesight or under low light conditions, may have difficulty in correctly orienting the tub for attachment onto the cradle.

SUMMARY OF THE INVENTION

One aspect of the invention relates to a low cost humidifier tub that allows increased moisture pickup by the air flow while minimizing pressure loss when the air travels through the tub.

Another aspect of the invention relates to a humidifier tub that decreases or prevents the chances of water flowing back into the flow generator if the tub is overfilled. In one example, a humidifier includes a humidifier tub including an air inlet and an air outlet. The air outlet has an exit port having a lower-most portion that is positioned in a plane disposed below a lower-most portion of the air inlet. Further, the outlet of the humidifier is preferably lower than the outlet of the flow generator. Thus, over-filling will result in water emerging from the outlet rather than through the inlet and possibly into the flow generator. In addition or in the alternative, the inlet may be in the form of an inlet tube that is angled relative to horizontal such that water is guided from the inlet tube towards the water chamber.

Another aspect of the invention relates to a humidifier tub that provides a user guidance structure/system used during attachment of the tub to the heating cradle. The guidance structure may include generally flat converging side walls that provide guidance when inserting the tub into the humidifier unit/cradle.

Another aspect of the invention relates to a humidifier tub that is easy to manufacture (e.g., via molding) and/or requires simplified tooling.

Another aspect of the invention relates to a humidifier tub that is compact in size yet delivers appropriate moisture content to the flow of air.

Another aspect relates to a humidifier tub having a shape that reduces pressure loss.

Another aspect of the invention relates to a humidifier including a humidifier tub including an air inlet and an air outlet. The air outlet has an exit port positioned in a plane disposed below the air inlet. A base plate is provided to a bottom of the humidifier tub. The base plate and humidifier tub define a water chamber adapted to receive a volume of water. The humidifier tub includes a guidance structure adapted to direct air entering the humidifier tub via the air inlet to swirl downwardly and around within the humidifier tub before exiting the exit port.

Another aspect of the invention relates to a humidifier tub for a humidifier. The humidifier tub includes an upper wall and a cylindrical or substantially conical side wall defining a water chamber, an air inlet, an air outlet, and a curved baffle provided within the water chamber. The curved baffle extends downwardly from the upper wall and provides a concave surface positioned between the air inlet and the air outlet.

Yet another aspect of the invention relates to a method of humidifying air including providing a water chamber having an air inlet and an air outlet, directing air entering the water chamber via the air inlet in a downward direction before exiting the air outlet, and directing air entering the water chamber via the air inlet in a spiral direction down to the water surface before exiting the air outlet.

Yet another aspect of the invention relates to a humidifier including a humidifier tub including an air inlet and an air outlet and a base plate provided to a bottom of the humidifier tub. The base plate and humidifier tub define a water chamber adapted to receive a volume of water. The humidifier tub includes a guidance structure adapted to smoothly direct air entering the humidifier tub via the air inlet to a surface of the water before exiting via the air outlet.

Still another aspect of the invention relates to a humidifier tub for a humidifier including a first component defining a first partial tubular air inlet flow path portion and a second component coupled to the first component and defining a second partial tubular air inlet flow path portion. The first and second partial tubular air inlet flow path portions cooperate to define a composite tubular air inlet flow path that directs incoming air in a generally circular manner down and around within the tub.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 1 is a perspective view of a CPAP device including a humidifier tub according to an embodiment of the invention;

FIGS. 9-10 are perspective views of a cradle and user guidance system according to an embodiment of the invention;

FIGS. 11-12 are perspective views of a cradle and user guidance system according to another embodiment of the invention;

DETAILED DESCRIPTION OF ILLUSTRATED EMBODIMENTS

1. Humidifier Tub

Figure 2A:
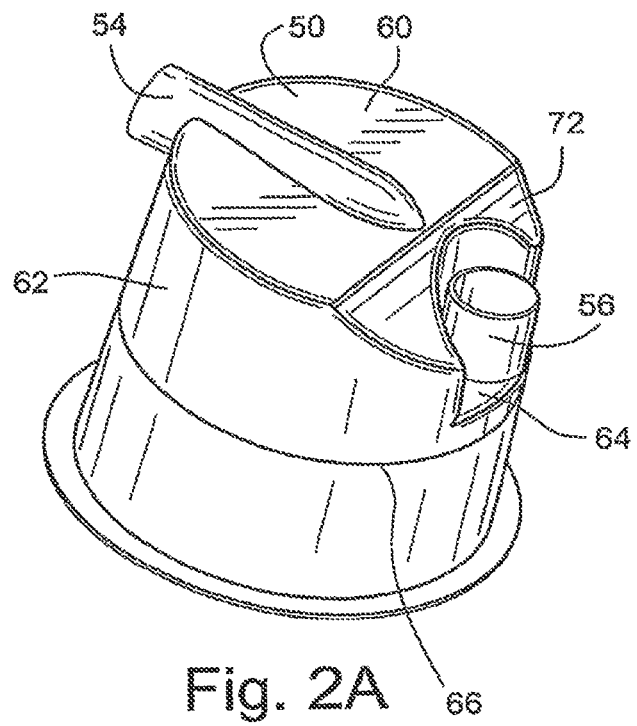
FIG. 2A is a perspective view of the humidifier tub shown in FIG. 1 removed from the flow generator of the CPAP device.

FIG. 1 illustrates a humidifier tub 50 for a humidifier 30 of a CPAP device 10 according to an embodiment of the present invention. As illustrated, the CPAP device 10 includes a flow generator 20 and a humidifier 30 provided to the flow generator 20.

The flow generator 20 includes a housing 22 and a blower (not shown) supported within the housing 22. As is known in the art, the blower is operable to draw a supply of air into the housing 22 through one or more intake openings and provide a pressurized flow of air at an outlet 24. In an embodiment, the flow generator 20 may be structured and controlled such as the flow generator described in U.S. Patent Application No. 60/707,951, entitled "Low Cost CPAP Flow Generator and Humidifier Assembly," filed Aug. 15, 2005, the contents of which are incorporated in its entirety by reference herein.

The humidifier 30 includes the humidifier tub 50, which includes a base plate 52 sealed to the bottom of the tub 50. Humidifier 30 includes or is associated with a heating element that may be provided to a cradle 40 (FIG. 9). The tub 50 includes an inlet 54 adapted to be connected to the outlet 24 of the flow generator 20, and an outlet 56 adapted to be connected to an air delivery conduit. The air delivery conduit includes one end coupled to the outlet 56 of the tub 50 and an opposite end coupled to a patient interface. The patient interface comfortably engages the patient's face and provides a seal. The patient interface may have any suitable configuration as is known in the art, e.g., full-face mask, nasal mask, oro-nasal mask, mouth mask, nasal prongs, etc.

The tub 50 and base plate 52 define a chamber 58 (see FIG. 3) that is adapted to receive a volume of water, e.g., several hundred milliliters. The inlet 54 and the outlet 56 are both communicated with the chamber 58. In use, a supply of pressurized air from the flow generator 20 enters the inlet 54 of the tub 50 and collects moisture through contact with the water within the tub 50 before continuing on to the outlet 56 and to the patient via the air delivery conduit.

1.1 Air Inlet Flow Tube and Air Outlet Flow Tube

Figure 2B:
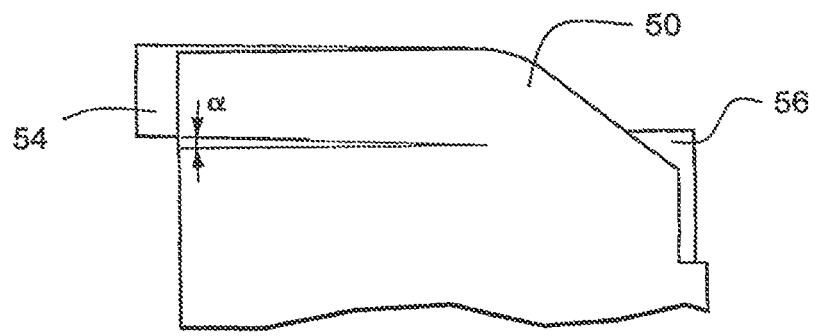
FIG. 2B is a side view of part of the humidifier tub shown in FIG. 2A.

As best shown in FIGS. 2A and 2B, the humidifier tub 50 has a substantially cylindrically-shaped or curved side wall 62 and may have a slight tapering towards the upper wall or lid 60. In an embodiment, the tub 50 is molded from a plastic material, e.g., polypropylene or other clear materials, and the tapering facilitates the ejection of the molded tub from the manufacturing tool. The tub 50 is preferably made from polypropylene to maintain a low cost although other suitable plastics may be used.

Figure 2D:
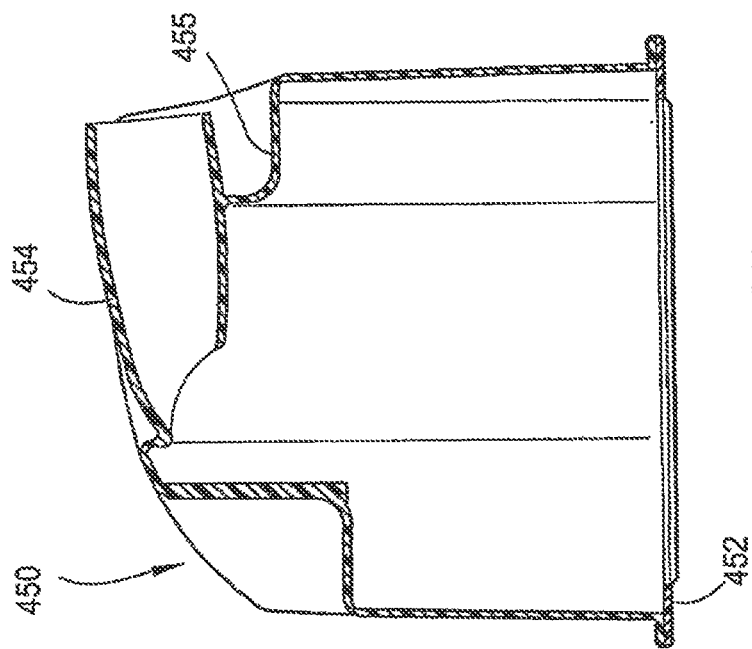
FIG. 2D is a cross-sectional view through line 2D-2D of FIG. 2C.
Figure 2C:
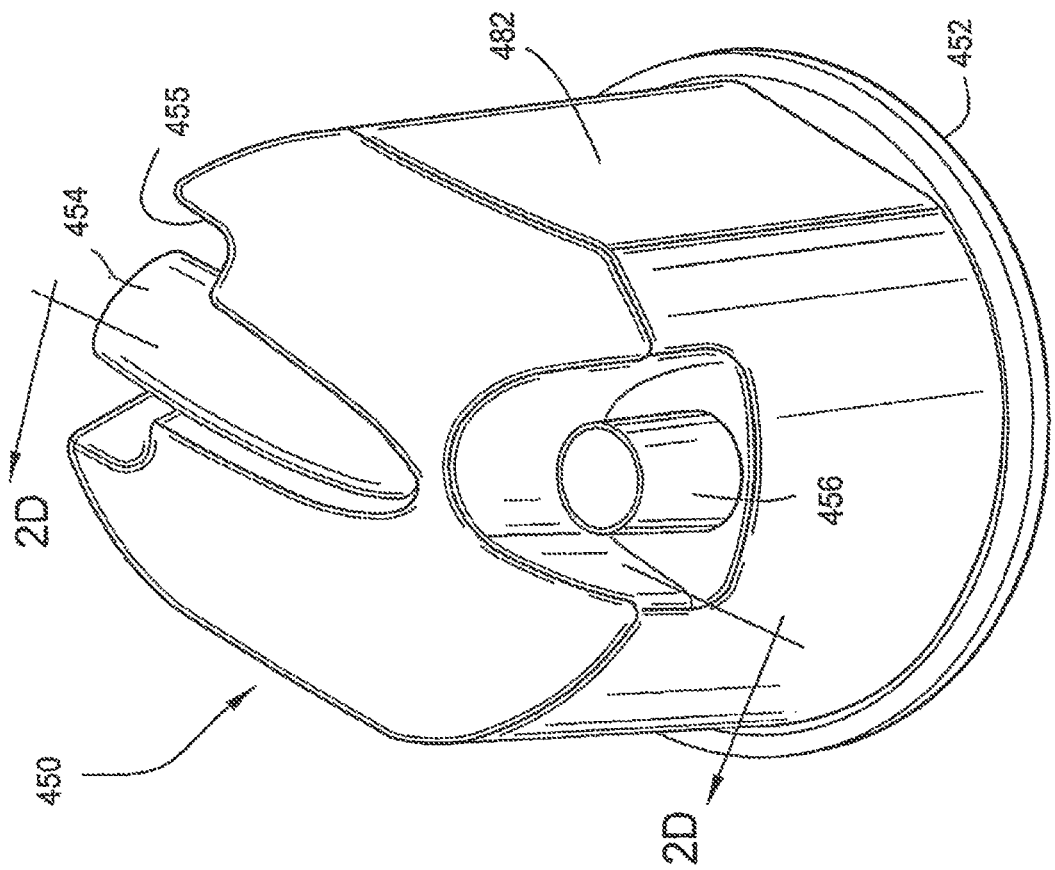
FIG. 2C is a perspective view of a humidifier tub according to another embodiment of the present invention.

FIGS. 2C and 2D illustrate a humidifier tub 450 substantially similar to the humidifier tub 50. As illustrated, the tub 450 includes an inlet 454 and an outlet 456, and a base plate 452 is sealed to the bottom of the tub 450. In contrast to tub 50, the tub 450 includes a recess 455 surrounding the inlet 454 that may facilitate connection with the flow generator 20.

As shown in FIGS. 2A, 2B, 3, and 4, the inlet 54 is in the form of an air inlet flow tube and the outlet 56 is in the form of an air outlet flow tube. In the illustrated embodiment, the air inlet flow tube 54 enters the tub 50 at the upper edge of the sidewall 62. The air inlet flow tube 54 is centrally located and extends towards the center of the tub 50. As illustrated, at least a portion of the air inlet flow tube 54 is formed within the lid 60 of the tub 50, such that the upper surface of the air inlet flow tube 54 forms a part of the lid 60. The length of the air inlet flow tube 54 may vary and may extend beyond the center of the tub 50. Also, the air inlet flow tube 54 may be precisely horizontally oriented, although preferably the air inlet flow tube 54 is positioned to have a slight downward angle across its longitudinal axis, e.g., 0°-15° or about 3°-5° slight downward angle α as shown in FIG. 2B. Of course, other angles are contemplated and the angle may be slightly upwardly angled.

In the illustrated embodiment, the air outlet flow tube 56 is generally vertically oriented or generally transverse to the air inlet flow tube 54. As illustrated, the air outlet flow tube 56 is located in a recessed portion 64 of the tub 50 on the opposing side of the tub 50 to the air inlet flow tube 54. The recessed portion 64 is positioned slightly above a suggested maximum water filling level (indicated by water filling indication mark 66 in FIG. 2A). The height to which the air outlet flow tube 56 extends from the base of the tub 50 is less than the final height to which the bottom edge of the air inlet flow tube 54 extends from the base of the tub 50. That is, the air outlet flow tube 56 has an exit port that is positioned in a plane disposed below the air inlet flow tube 54. This arrangement advantageously prevents water from flowing back into the flow generator 20 via the air inlet flow tube 54. For example, if the tub 50 is filled above the water filling indication mark 66, the water will simply flow back out the air outlet flow tube 56 rather than into the air inlet flow tube 54 and consequently into the flow generator 20 via outlet 24.

Figure 7A:
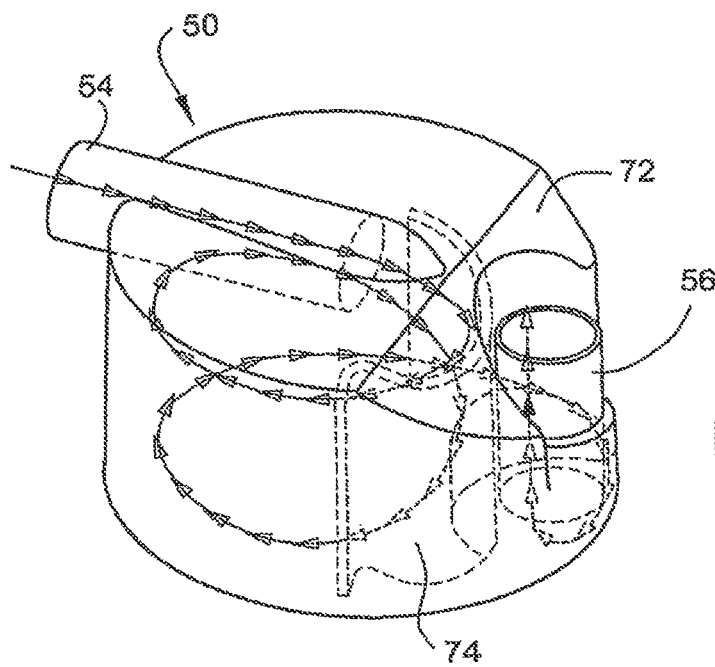
FIG. 7A is a perspective view of a Computational Fluid Dynamic (CFD) simulation of the humidifier tub air flow shown in FIGS. 3-4.
Figure 7B:
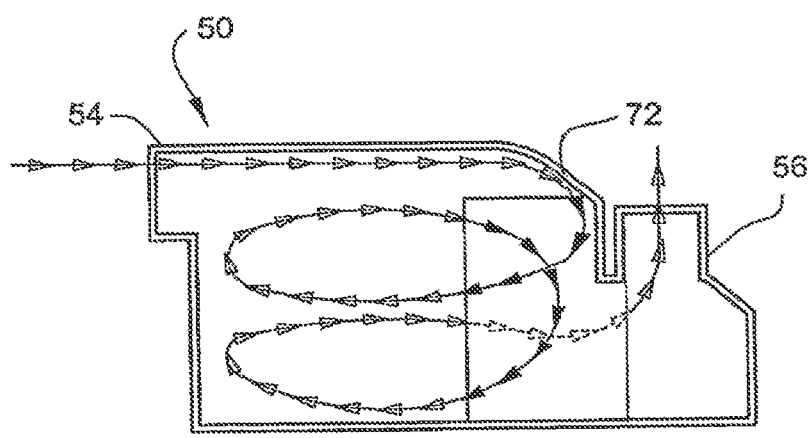
FIG. 7B is a side view of a CFD simulation of the humidifier tub air flow shown in FIGS. 3-4.
Figure 7C:
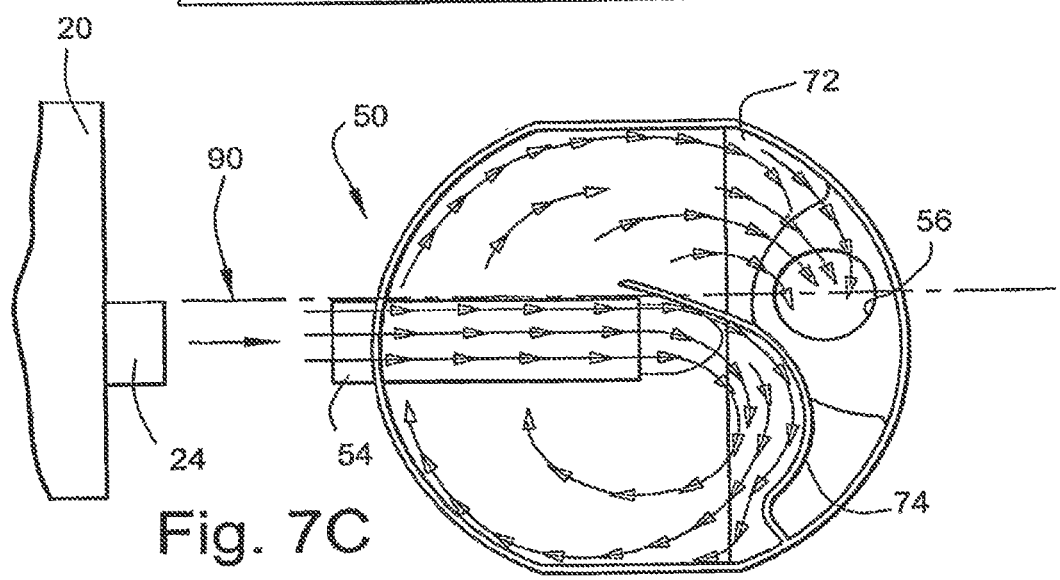
FIG. 7C is a top view of a CFD simulation of the humidifier tub air flow shown in FIGS. 3-4.

In the illustrated embodiment, the air outlet flow tube 56 is substantially aligned with a central axis 90 of the CPAP device 10 extending through the flow generator 20 and the humidifier tub 50 as shown in FIGS. 1 and 7C. Also, the air outlet 24 of the flow generator 20 and the air inlet flow tube 54 of the humidifier tub 50 are offset from the axis 90. This combination of the humidifier tub air outlet flow tube 56 location with the extended air inlet flow tube 54, the potential for water spillback into the flow generator 20 is greatly reduced should the CPAP device 10 be tilted through a large angle, such as 60° or greater, in any of the four orientations, i.e., rearwards, forwards, left or right. However, the axis 90, the air outlet flow tube 56, the air inlet flow tube 54 of the humidifier tub 50, and/or the air outlet 24 of the flow generator 20 may be aligned with one another or offset from one another in any suitable manner 1.2 Moisture Pickup and Airflow To increase moisture pickup and minimize pressure loss, the interior of the tub 50 is designed to encourage smooth air flow that swirls down and around the tub 50 reaching the water surface before exiting out of the air outlet flow tube 56. This flow configuration is achieved by providing a guidance structure 70 (also referred to as a swirling mechanism) within the tub 50.

Figure 3:
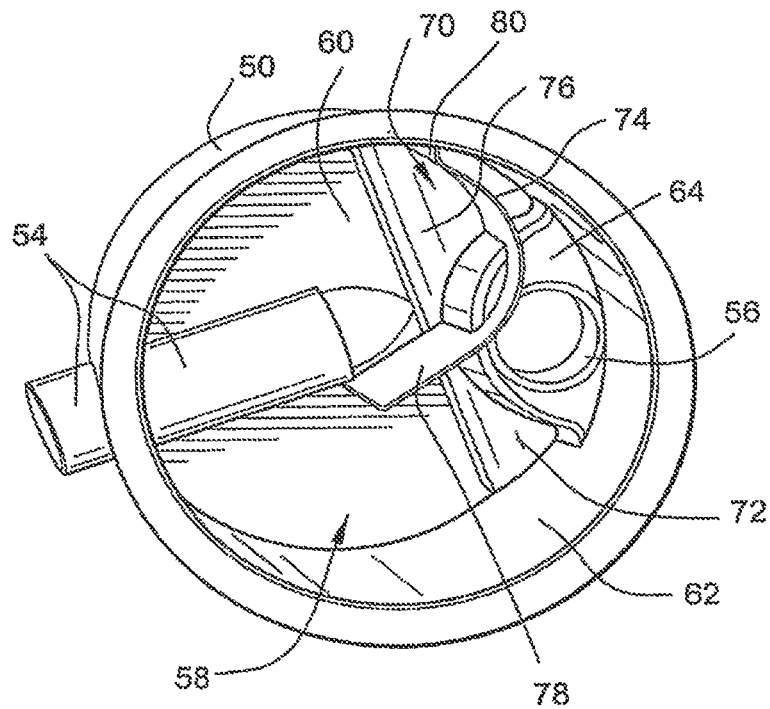
FIG. 3 is a perspective view of the inside of the humidifier tub shown in FIG. 2A.
Figure 4:
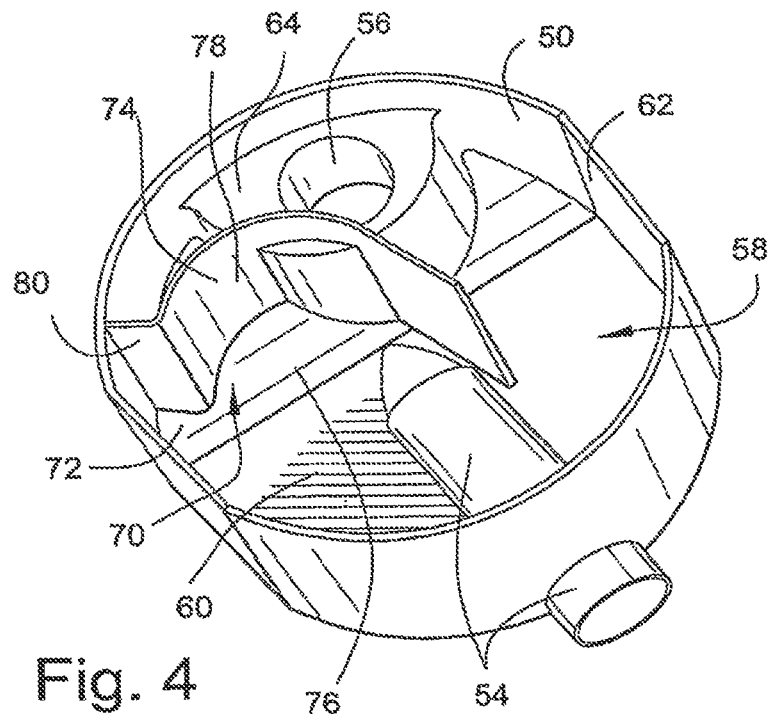
FIG. 4 is another perspective view of the inside of the humidifier tub shown in FIG. 2A.

As best shown in FIGS. 3 and 4, the guidance structure 70 includes a chamfered wall portion 72 and a curved baffle 74. As illustrated, the chamfered wall portion 72 is incorporated into the lid 60 of the tub. The chamfered wall portion 72 begins after the outlet end of the air inlet flow tube 54 and extends downwardly towards the air outlet flow tube 56. The chamfered wall portion 72 provides a chamfered face or inclined interior surface 76 positioned directly in front of incoming air from the air inlet flow tube 54. This configuration encourages the air flow to move downwardly towards the surface of the water within the tub 50.

The curved baffle 74 is provided within the interior of the tub 50 and extends downwardly from the lid 60. As illustrated, the curved baffle 74 protrudes past the bottom edge of the air inlet flow tube 54. In an embodiment, the curved baffle 74 may protrude to the water filling indication mark 66. However, the curved baffle 74 may have any suitable height, e.g., one end of the baffle may be longer than an opposing end of the baffle. Also, the curved baffle 74 includes a generally constant thickness in the illustrated embodiment. However, the thickness of the curved baffle 74 may vary, e.g., thickness may increase and/or decrease along its height and/or length. The curved baffle 74 provides a concave surface 78 positioned in front of the outlet end of air inlet flow tube 54.

The curved baffle 74 acts to deflect or force incoming air to travel over a larger surface area, thereby allowing increased moisturization of the flow of gas. The use of a curved baffle 74 having a concave surface 78 smoothly changes the direction of the air flow by gently guiding the air flow around the tub 50 in a swirling motion while limiting the loss of pressure. In contrast, sharp changes in direction cause the amount of pressure loss to be greater.

As shown in FIGS. 3 and 4, the curved baffle 74 includes an end portion 80 that is joined to the side wall 62 of the tub 50. This arrangement prevents air from flowing around this end portion 80 of the curved baffle 74. Alternatively, the end portion of the curved baffle may be spaced from the side wall of the tub.

1.2.1 Curved Baffle Spaced from Side Wall

Figure 5:
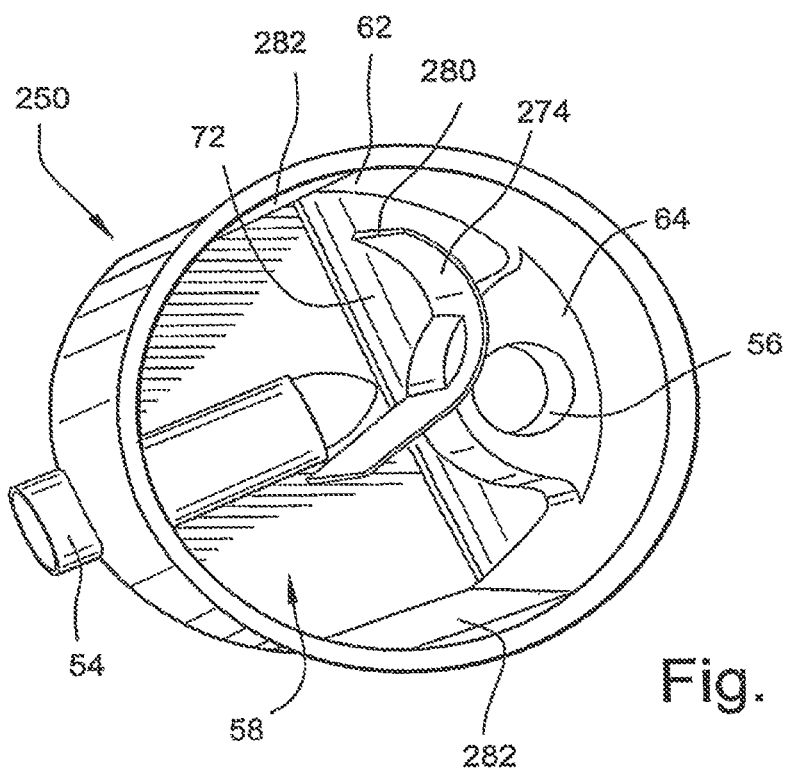
FIG. 5 is a perspective view of the inside of a humidifier tub according to another embodiment of the invention.
Figure 6:
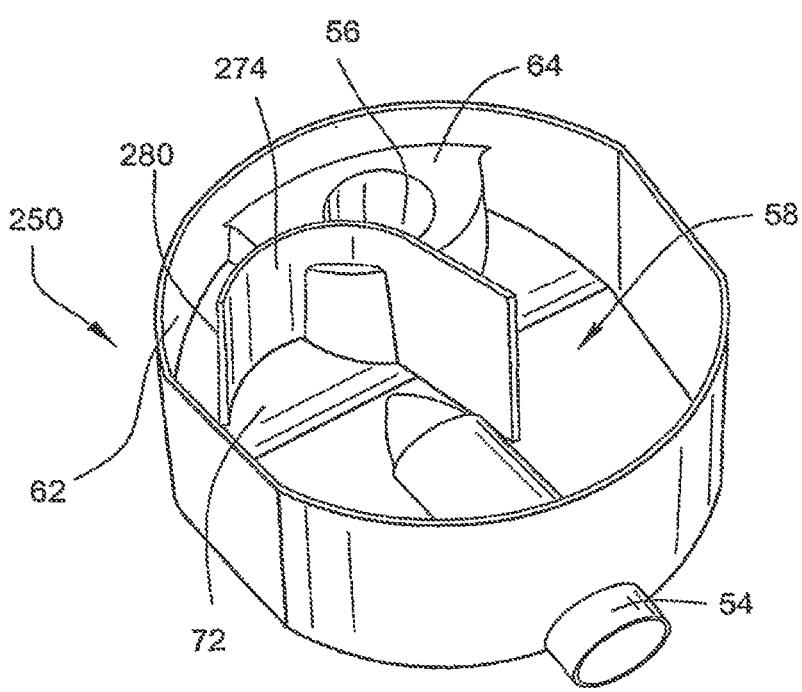
FIG. 6 is another perspective view of the inside of the humidifier tub shown in FIG. 5.

For example, FIGS. 5 and 6 illustrate a humidifier tub 250 according to another embodiment of the invention. In this embodiment, the tub 250 includes a curved baffle 274 wherein the end portion 280 of the curved baffle 274 is spaced from the side wall 62. That is, the end portion 280 ends at a distance from the side wall 62 to provide a gap between the end portion 280 and the side wall 62. This arrangement allows some circulating air to flow around the end portion 280 of the curved baffle 274. The remaining components of the tub 250 are similar to the tub 50 and indicated with similar reference numerals.

1.2.2 Air Flow Motion

The combination of the chamfered wall portion 72 and the curved baffle 74, 274 (and possibly the downwardly inclined air inlet flow tube 54, 254) directs the air flow in a helical motion in both a spiral and downwards direction towards the surface of the water in the tub 50. Specifically, the concave surface 78 of the curved baffle 74 is positioned in front of the outlet end of air inlet flow tube 54 to direct incoming air in a spiraling or swirling motion. In addition, the inclined interior surface 76 of the chamfered wall portion 72 is positioned in front of the outlet end of air inlet flow tube 54 to direct incoming air in a downward motion towards the surface of the water. Thus, the combination of the concave surface 78 and the inclined interior surface 76 direct incoming air in both a spiraling and downward motion, also referred to as helical motion. That is, the air has a spiraling motion with an axial component.

The chamfered wall portion 72 and the curved baffle 74 may be positioned such that the incoming air is directed in a spiral motion before being directed in a downward motion. Alternatively, the chamfered wall portion 72 and the curved baffle 74 may be positioned such that the incoming air is directed in a downward motion before being directed in a spiral motion. In addition, the spiral and downward motion may occur substantially simultaneously.

This helical motion enhances moisture pickup. For example, the tub 50 may improve moisture pickup by approximately 25% or greater compared to prior art tubs.

1.2.3 Computational Fluid Dynamic (CFD) Analysis

Computational fluid dynamic (CFD) analysis of 3D models of the two above-described tubs 50 and 250 having different baffle designs were performed with a volume flow of about 100 L/min applied at the air inlet flow tube 54 and a pressure of about 12 cm $H_2O$ at the air outlet flow tube 56. In the illustrated embodiment, the two tubs 50 and 250 have substantially similar exterior surfaces. In contrast, the tub 50 includes an end portion 80 of the baffle 74 that is joined to the side wall 62, while the tub 250 includes an end portion 280 of the baffle 274 that is spaced from the side wall 62 to provide a gap.

The pressure drop between air inlet flow tube 54 and air outlet flow tube 56 in cm$H_2O$ is shown in the table below. As illustrated, the pressure drop for the tub 250 is slightly smaller than the pressure drop for the tub 50.

| Tub Option | Pressure Drop Inlet-Outlet (cm $H_2O$) |
| --- | --- |
| 1-Baffle 74 joined to side wall 62 | 0.77 |
| 2-Gap between baffle 274 and side wall 62 | 0.69 |

Figure 8A:
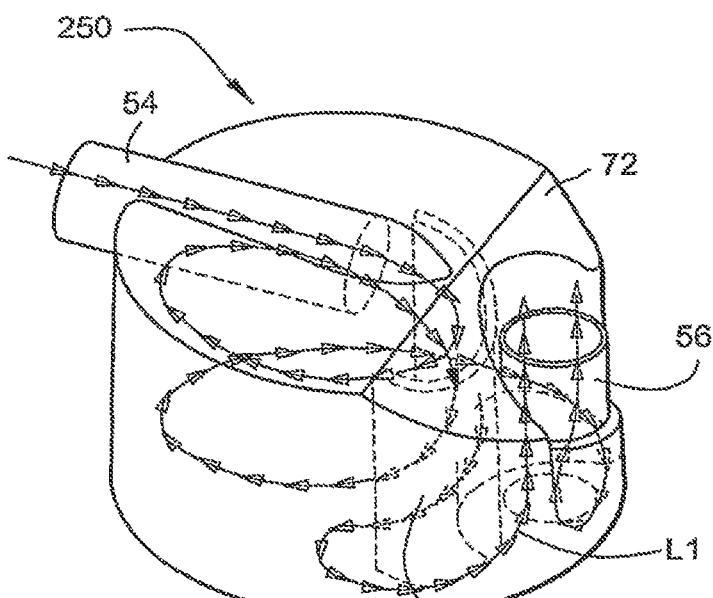
FIG. 8A is a perspective view of a CFD simulation of the humidifier tub air flow shown in FIGS. 5-6.
Figure 8B:
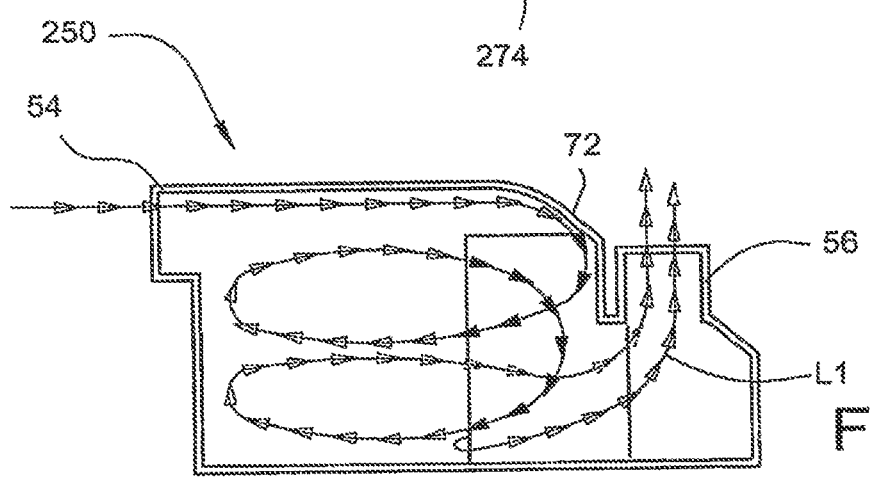
FIG. 8B is a side view of a CFD simulation of the humidifier tub air flow shown in FIGS. 5-6.
Figure 8C:
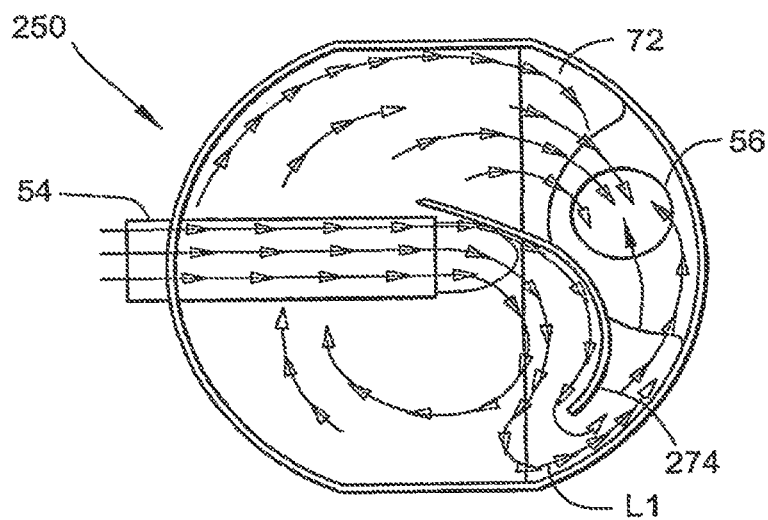
FIG. 8C is a top view of a CPD simulation of the humidifier tub air flow shown in FIGS. 5-6.

Air flow lines of the tub 50 are shown in FIGS. 7A-7C, and air flow lines of the tub 250 are shown in FIGS. 8A-8C. As illustrated, each of the tubs 50, 250 presents a characteristic of swirling flow as the air meets the respective curved baffle 74, 274 and downward flow as the air meets the chamfered wall portion 72 as described above. As best shown in FIGS. 8A and 8C, the tub 250 allows some of the air flow, indicated as Li, to take a shortcut path behind the baffle 274 to the air outlet flow tube 56 via the gap between the baffle 274 and the side wall 62. This arrangement results in a slightly smaller pressure drop for the tub 250 due to less flow restriction.

Also, the velocity of the air flow is similar for both tubs 50, 250 with the velocity of the air flow within the air inlet and air outlet flow tubes 54, 56 being substantially higher than the velocity within the tub interior. Due to different baffle designs, the localized velocity in the air inlet flow tube 54 is slightly higher for the tub 50.

Further benefits of providing better mixing of air and moisture pickup include a reduced water temperature for a given delivered air moisture content, which results in less electrical energy usage by the heater element and lower casing temperature. The reduced pressure loss means that the motor power of the flow generator 20 does not need to increase to compensate for this pressure loss. This saves motor power by lowering motor speed, which also results in reduced noise levels.

The baffle 74, 274 also prevents short-circuiting of the air flow from the air inlet flow tube 54 directly to the air outlet flow tube 56. The length of the baffle 74, 274 may vary, but its configuration and positioning provide a barrier between the air inlet and air outlet flow tubes 54, 56 and encourage swirling of the air entering the tub 50, 250.

In the illustrated embodiments, the baffle 74, 274 extends generally vertically into the tub interior. However, the baffle 74, 274 may be angled with respect to vertical such that it tilts away from the air coming towards it. This arrangement may provide a gentler change in air movement within the tub 50, 250 and consequently provide a lower pressure loss.

1.3 User Guidance System

The humidifier tub 50, 250, 450 may be designed to facilitate attachment to a cradle upon which it sits. The cradle is structured to support the humidifier 30 in an operative position with respect to the flow generator 20.

For example, FIGS. 9 and 10 illustrate a cradle 88 including a support surface 90 for supporting the flow generator 20 thereon and a support surface 92 for supporting the humidifier thereon. The support surface 92 may include a heating element for heating a heat conducting base of the humidifier. As illustrated, the tub 450 includes flattened sides 482 that slightly taper or converge towards the flow generator side of the tub 450 (also see flattened sides 282 of tub 250 in FIG. 5). The flattened sides 482 are configured to allow correct placement and alignment of the tub 450 on the cradle 88. The flattened sides 482 also identify the correct orientation of the tub 450. Specifically, the cradle 88 includes opposing side walls 94 that provide guiding surfaces 96 that engage the flattened sides 482 of the tub 450 to guide the tub 450 onto the cradle 88. Also, the side walls 94 provide slots 98 that guide the base of the humidifier onto the cradle 88. FIG. 10 illustrates the tub 450 aligned and positioned on the cradle 88. The flattened sides help to automatically align during docking. The flattened sides also provide easy and intuitive gripping surfaces for the patient.

Figure 12:
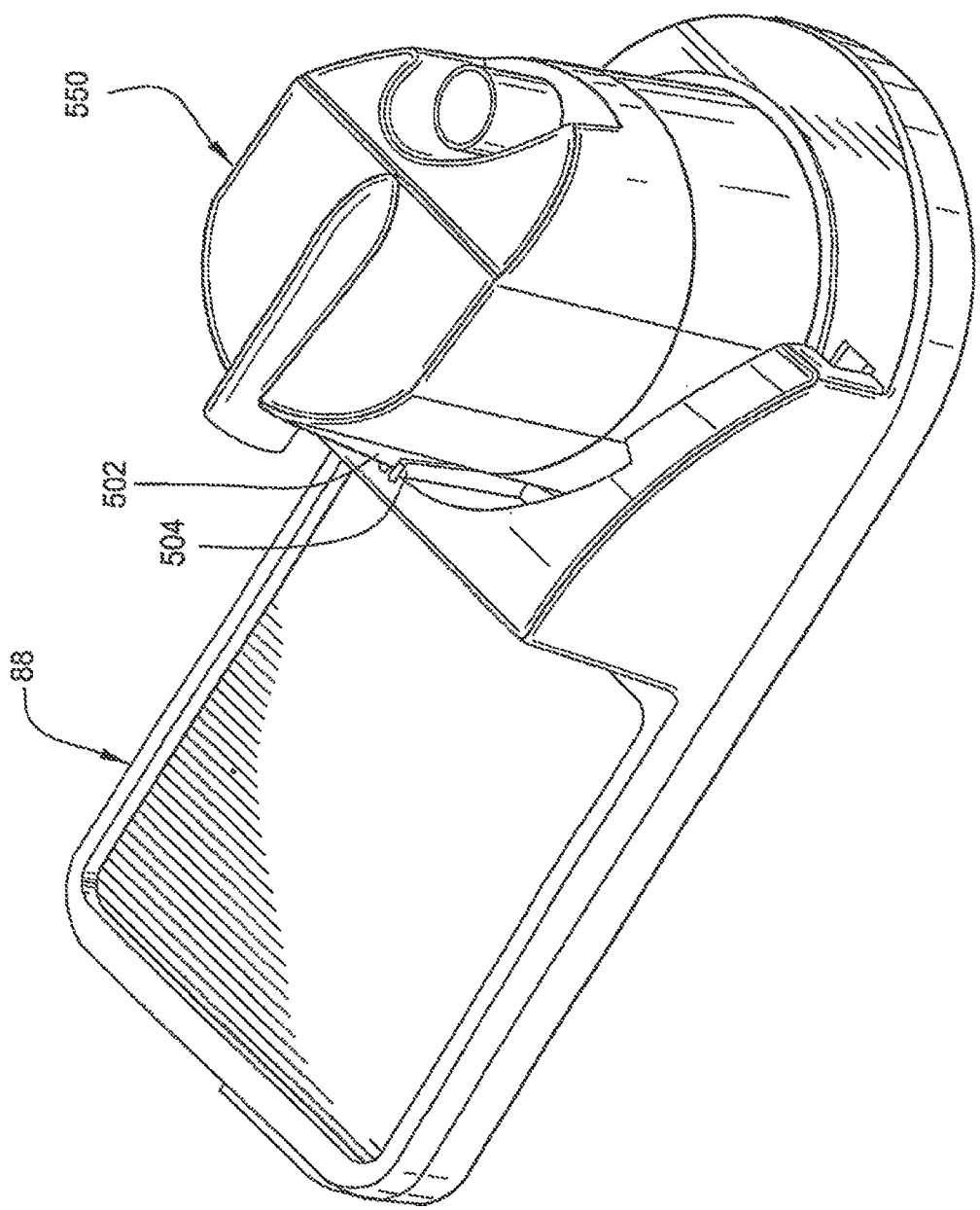

In an alternative embodiment or in addition to flattened sides, the tub 50, 250, 450 may include a vertical vane adapted to engage a correspondingly shaped slot or recess provided on the cradle 88. For example, FIGS. 11 and 12 illustrate a humidifier tub 550 including a vertical vane 502 located on the external surface on the flow generator side of the tub 550. The vertical vane 502 may be positioned perpendicularly to the side wall 562. The vertical vane 502 may be any suitable shape and is designed to fit or dock into a correspondingly shaped slot or recess 504 provided within the cradle 88 to ensure correct positioning of the tub 550 on the cradle 88. The opening of the corresponding slot or recess 504 on the cradle 88 may be designed to be wider at its periphery and become progressively narrow towards the final docking position. This allows more movement when initially aligning the tub vane 502 with the docking slot or recess 504 while ensuring the tub 550 is ultimately correctly docked. FIG. 12 illustrates the tub 550 aligned and positioned on the cradle 88 via the vane 502/slot 504 arrangement. However, it is noted that the reverse arrangement would also provide the same alignment benefits. Thus, the docking slot or recess 504 may be located on the humidifier tub 550 and the vane 502 may be located on the cradle 88 (not shown).

1.4 Base Plate

As noted above, a base plate 52, 452 is sealed to the bottom of the tub 50, 250, 450, 550 to define the chamber 58 that receives a volume of water (best shown in FIG. 2D). The base plate 52, 452 may be removably mounted to the tub 50, 250, 450, 550 to allow the tub 50, 250, 450, 550 to be cleaned. In an embodiment, the bottom of the tub 50, 250, 450, 550 and the base plate 52, 452 may have a "jam-jar" screw-on design.

Also, the base of the tub 50, 250, 450, 550 may include a silicone gasket or other suitable material for sealing to the base plate 52, 452. Further, the base plate 52, 452 may be in the form of a heat conducting base plate. Specifically, the base plate 52, 452 may be formed of a heat conducting material, e.g., stamped anodized thin gauge aluminum which is known to provide excellent heat conducting properties. The aluminum base plate 52, 452 may have a stamped rolled edge to clamp the silicone gasket used for sealing.

1.5 Humidifier Tub (S9) with S-Shaped Baffle

Figure 13:
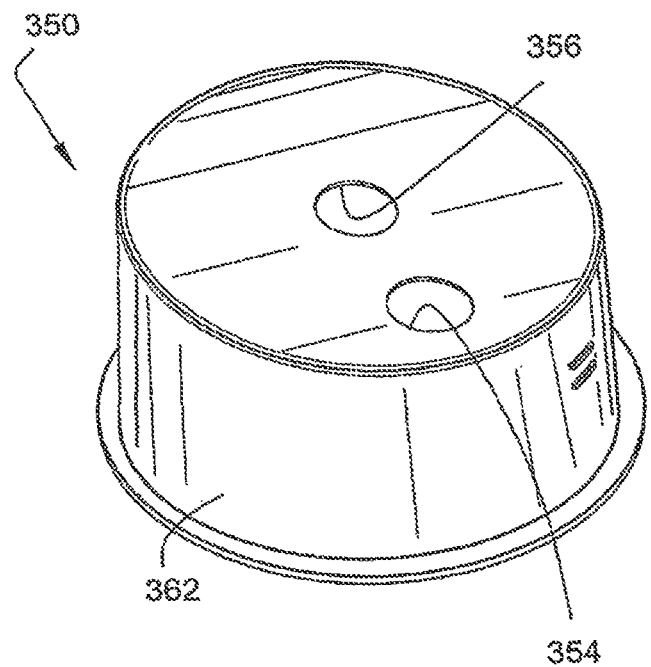
FIG. 13 is a perspective view of a humidifier tub according to yet another embodiment of the invention.
Figure 14:
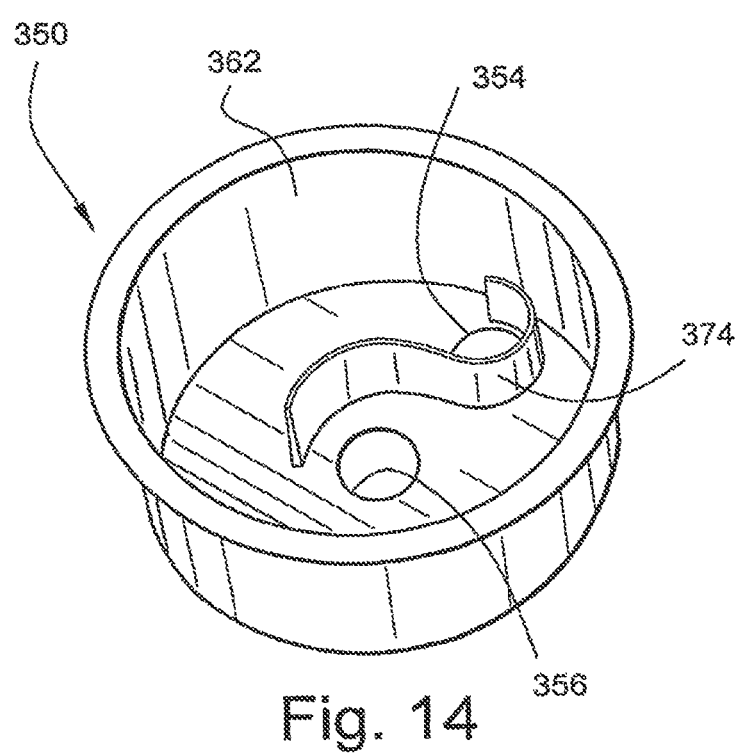
FIG. 14 is a perspective view of the inside of the humidifier tub shown in FIG. 13.
Figure 15:
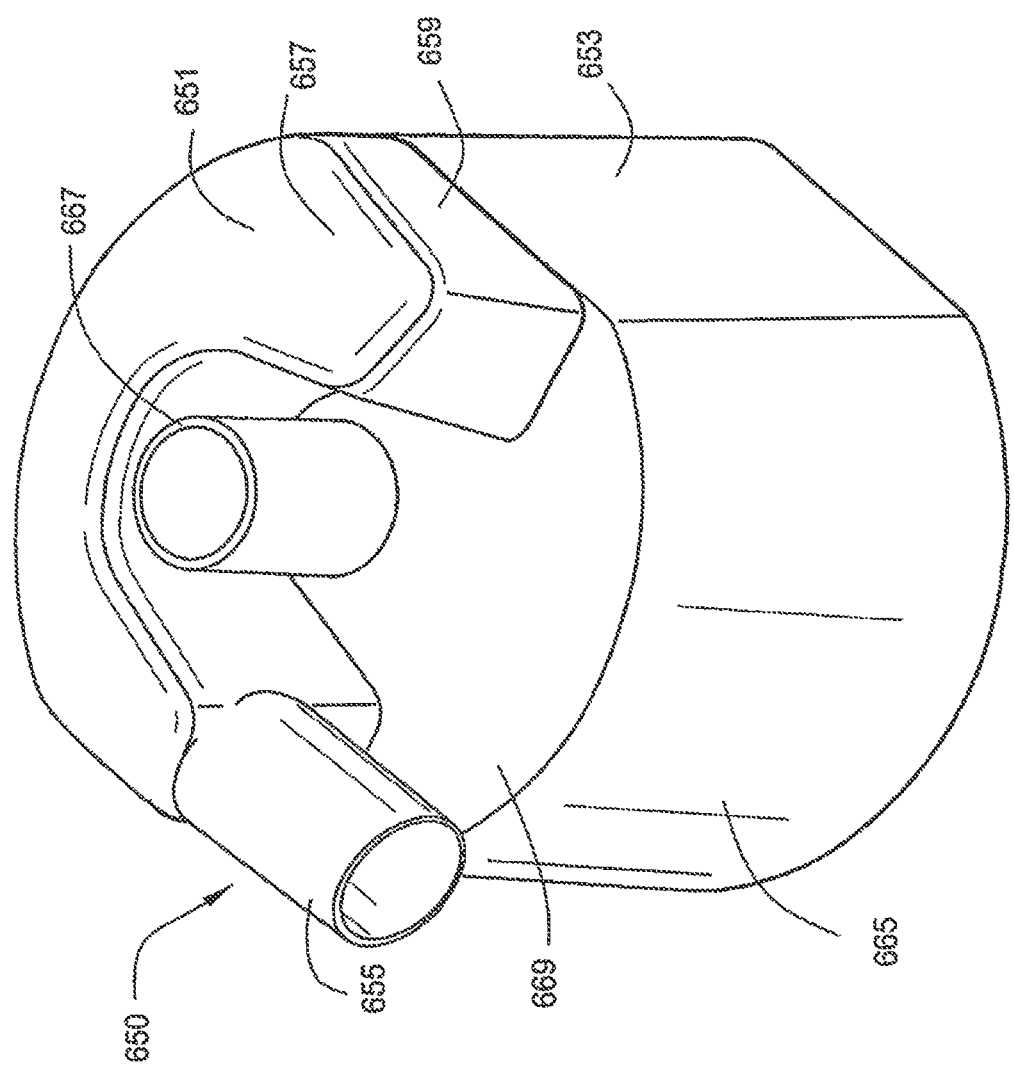
FIGS. 15-20 illustrate a humidifier tub according to yet another embodiment of the invention.
Figure 16:
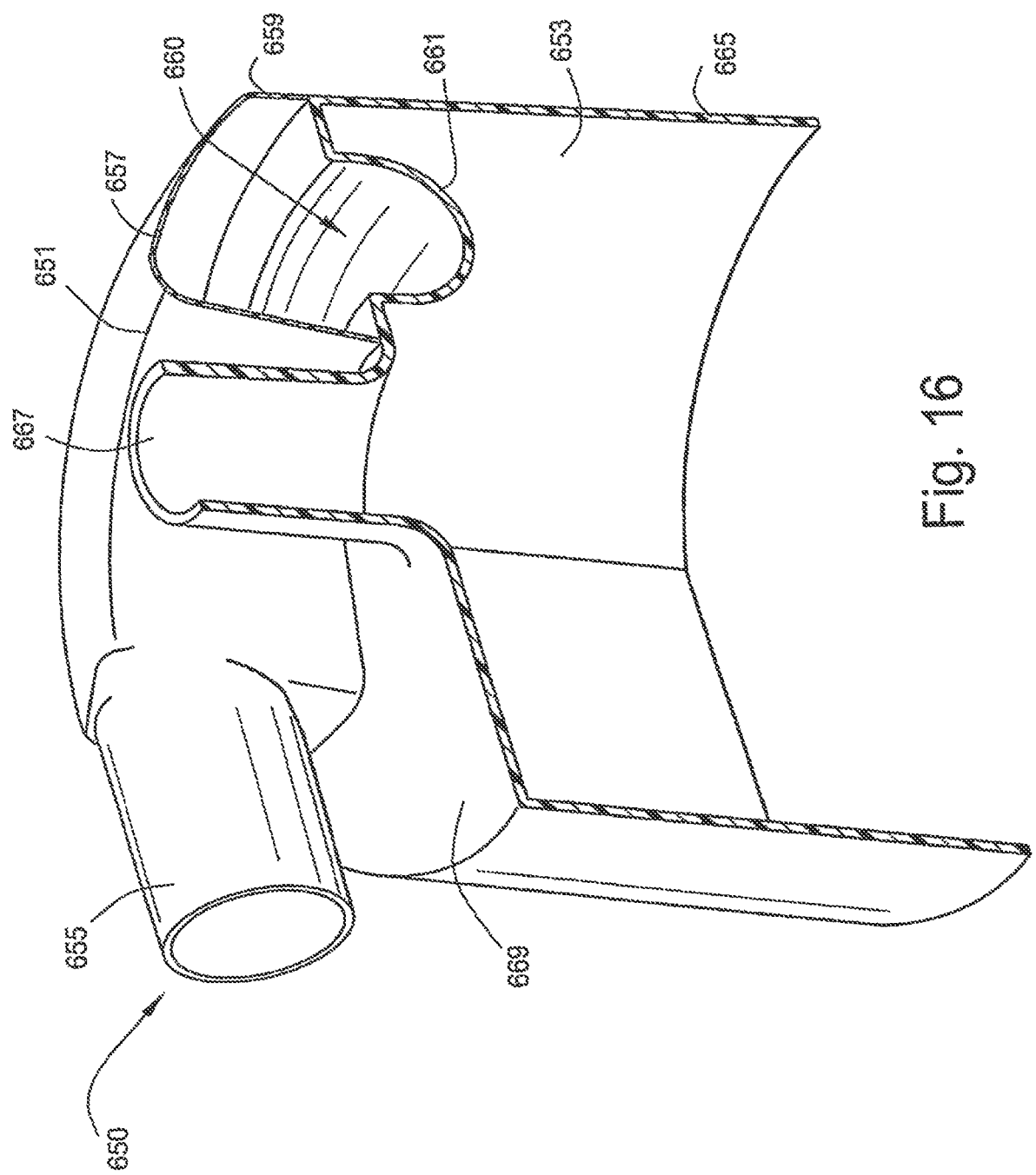

FIGS. 13 and 14 illustrate a humidifier tub 350 according to another embodiment of the invention. As illustrated, the humidifier tub 350 includes an air inlet 354 and an air outlet 356 provided through an upper wall of the tub 350. The air outlet 356 is located near a central axis of the tub 350. The air flow initially enters the tub 350 in a downwards direction towards the surface of the water.

The tub 350 also includes an S-shaped baffle 374 that curves around the outlet end of the air inlet 354 and then around the inlet end of the air outlet 356 as shown in FIG. 14. This arrangement provides a barrier between the air inlet 354 and air outlet 356 to prevent incoming air from short-circuiting directly to the air outlet 356. Further, the location of the outlet end of the air inlet 354 together with the baffle 374 and curve shaped side walls 362 encourage incoming air to swirl around and down into the tub 350 thereby providing excellent moisture pickup.

1.6 Alternative Embodiments of Humidifier Tub

Figure 17:
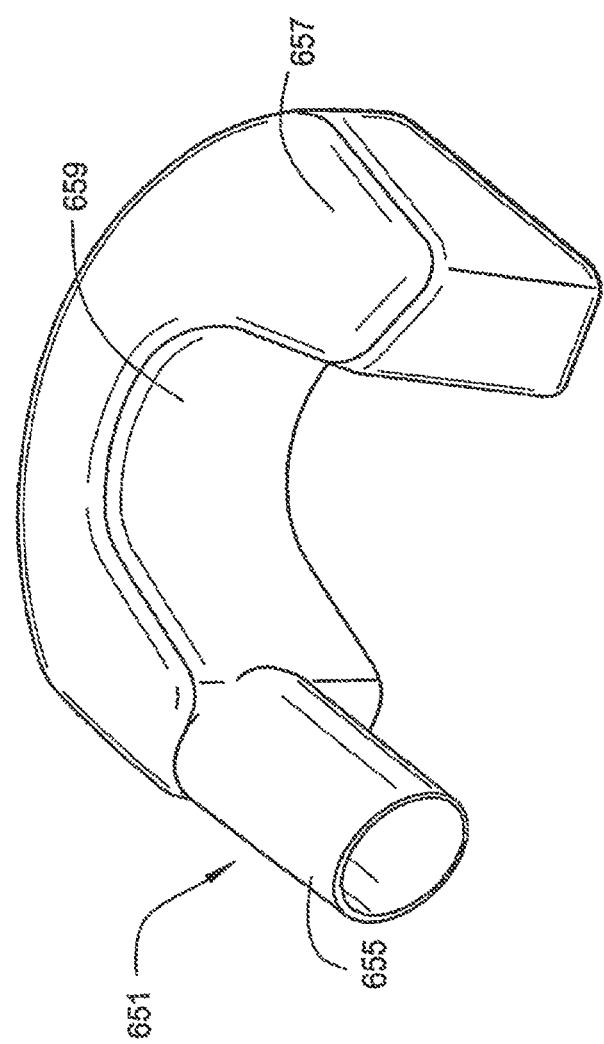
Figure 18:
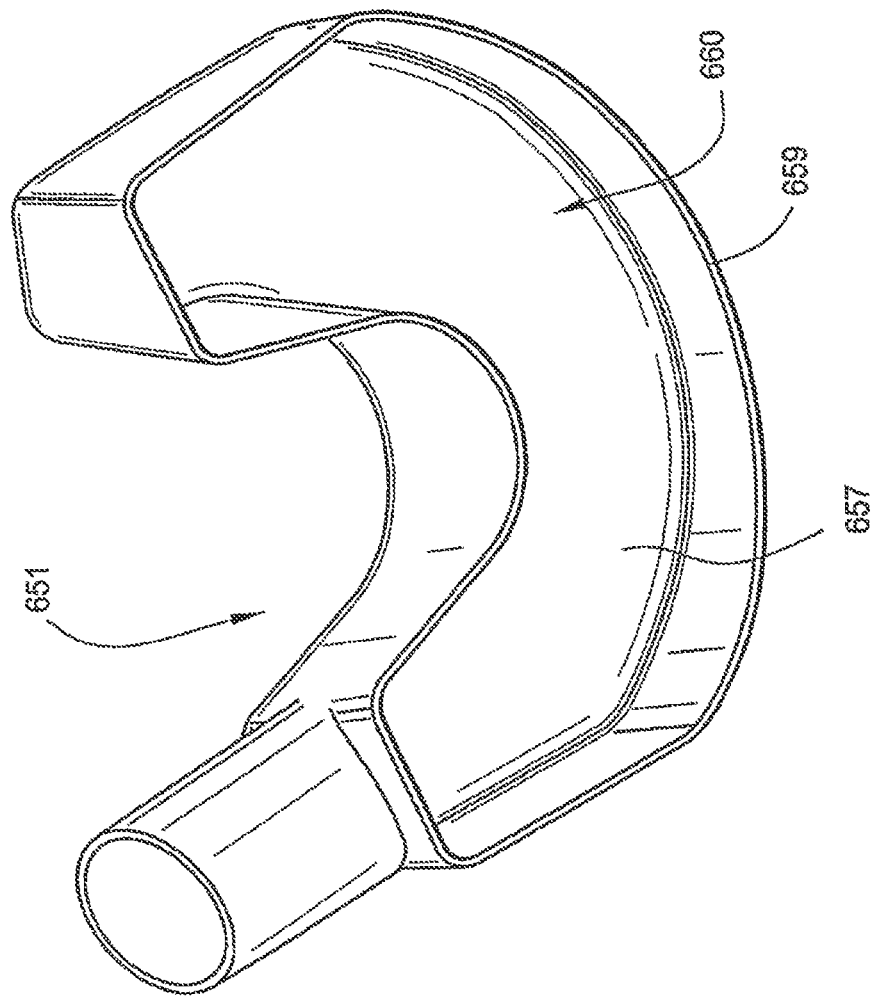
Figure 19:
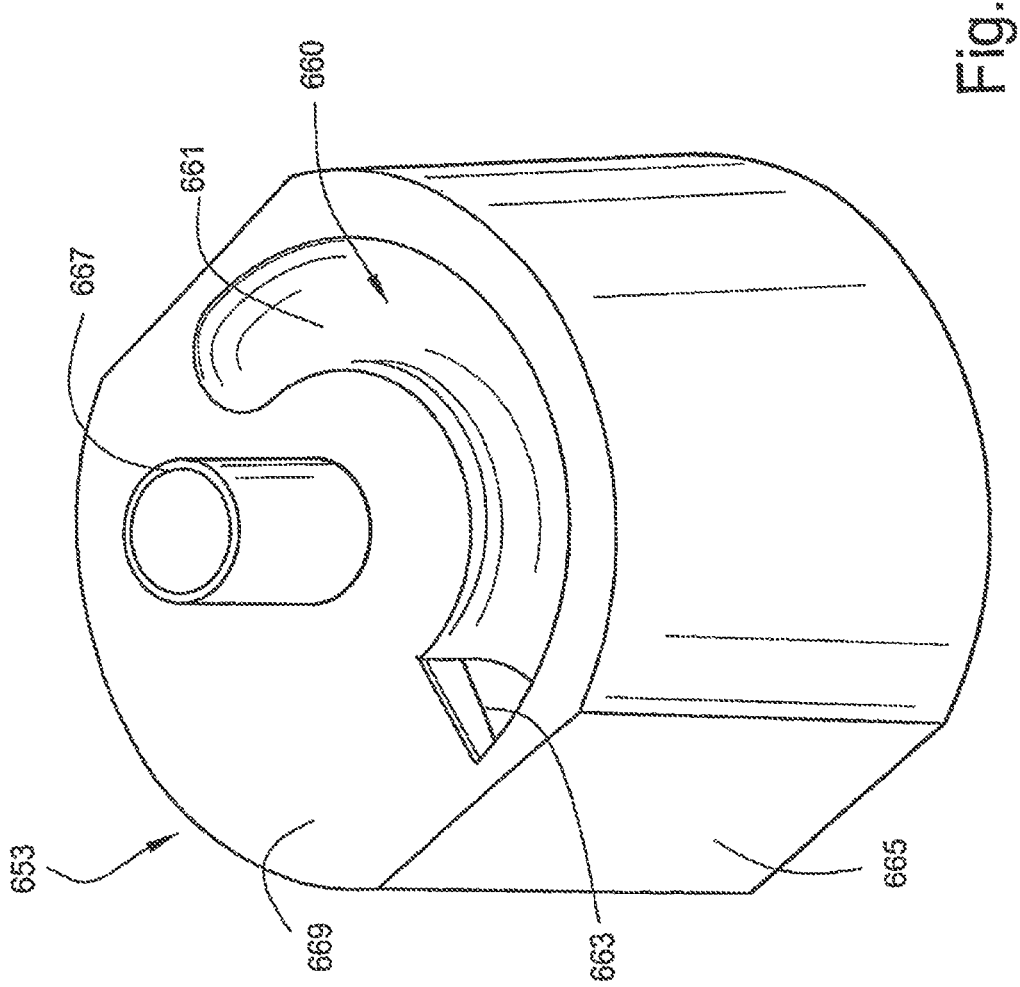
Figure 20:
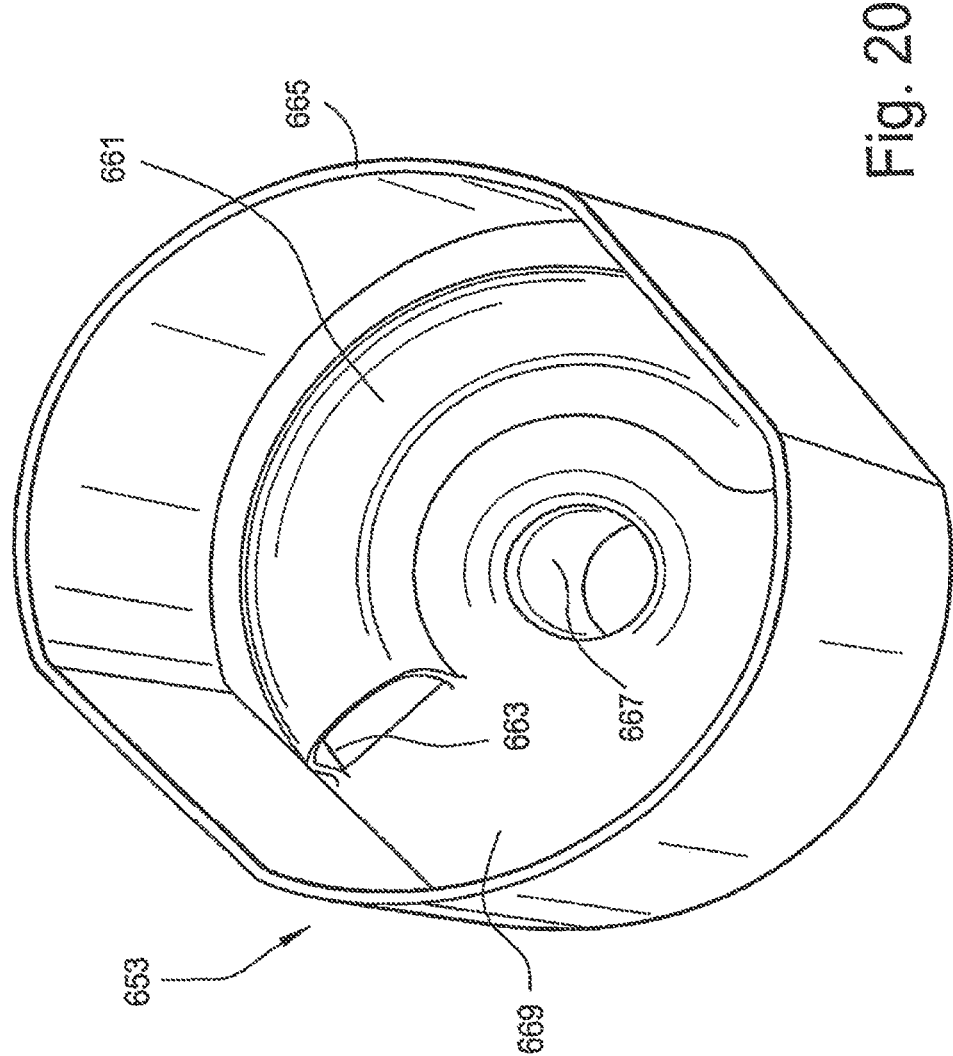
Figure 21:
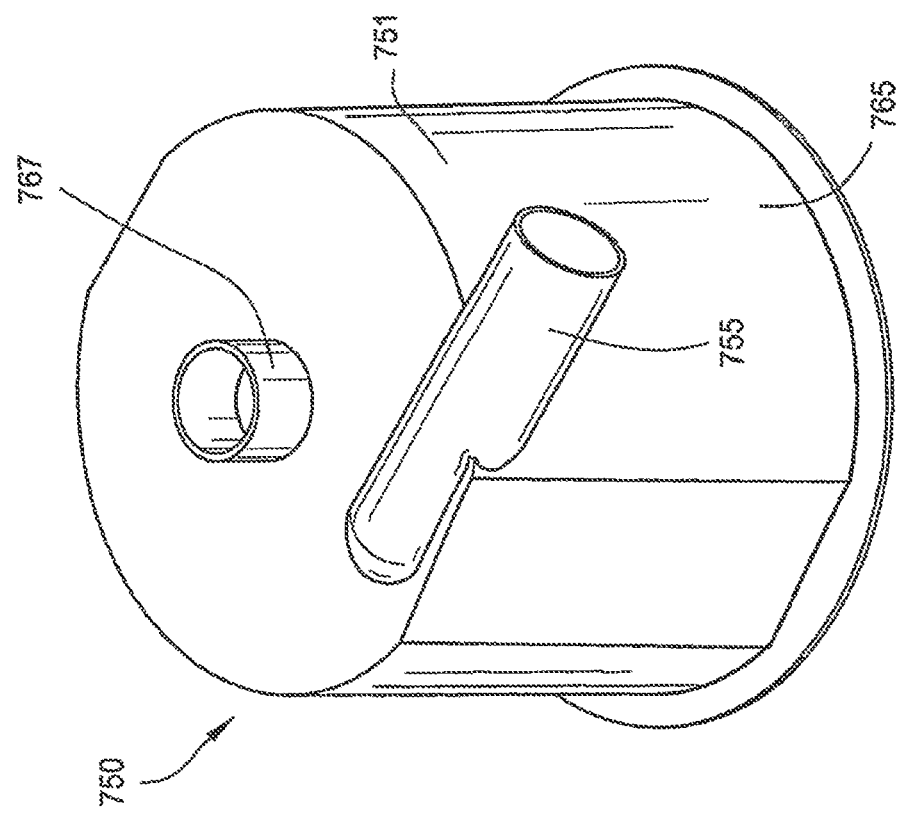
FIGS. 21-25 illustrate a humidifier tub according to still another embodiment of the invention.
Figure 22:
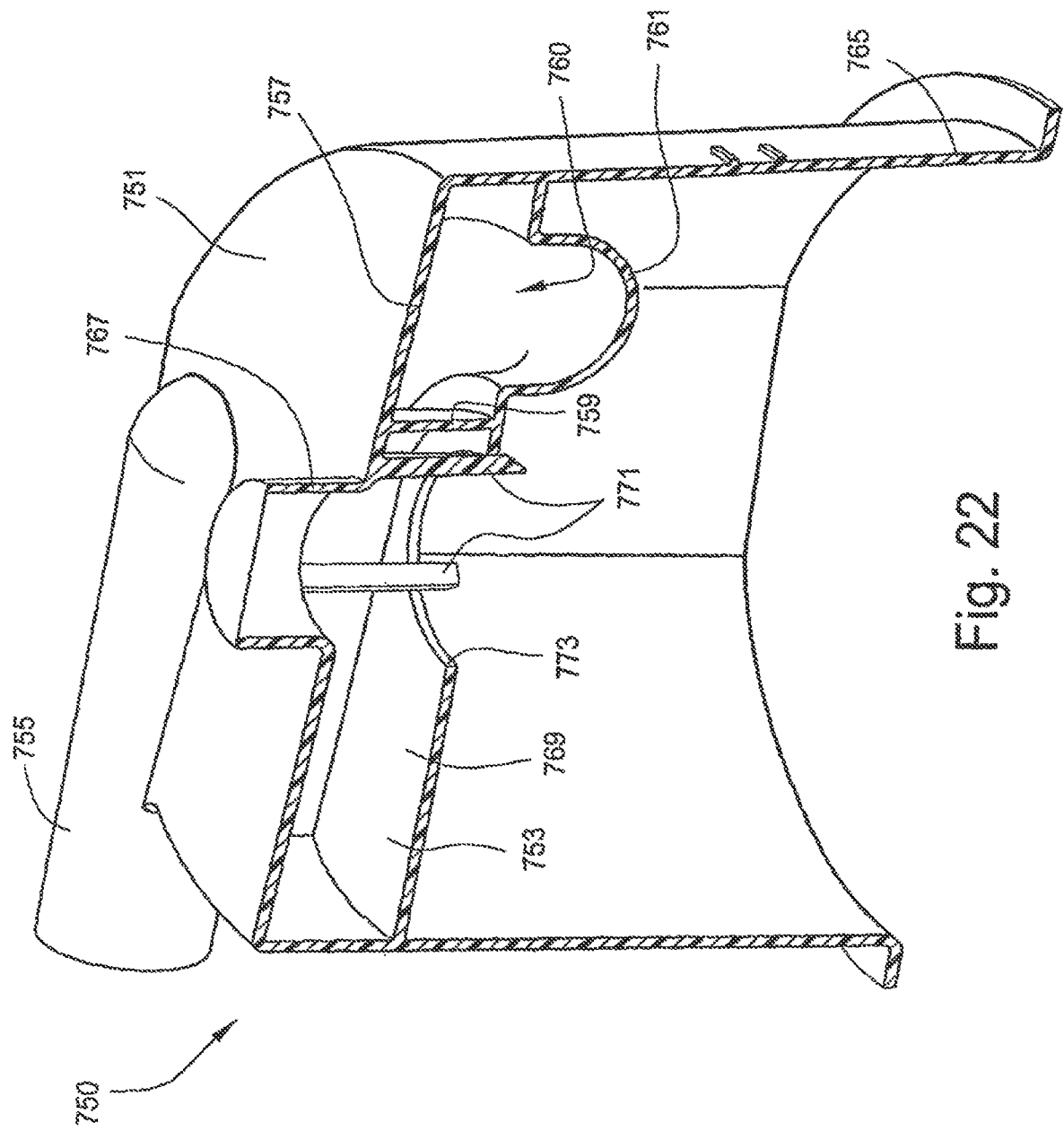

FIGS. 15-20 illustrate a humidifier tub 650 according to yet another embodiment of the invention. As illustrated, the humidifier tub 650 is constructed of two separate components that are coupled to one another. Specifically, the humidifier tub 650 includes an upper portion 651 and a lower portion 653 coupled to the upper portion 651. As best shown in FIGS. 17-18, the upper portion 651 includes an air inlet flow tube 655 and a roof 657 and side sections 659 of an air flow path 660 that directs incoming air down and around within the tub 650. As best shown in FIGS. 19-20, the lower portion 653 includes the floor or bottom section 661 of the air flow path 660 and provides a barrier 669 between the air flow path 660 and the bottom of the tub 650. An inlet opening 663 is provided that allows air to enter the chamber defined by the side wall 665 of the lower portion 653.

When the upper and lower portions 651, 653 of the tub 650 are coupled to one another (see FIGS. 15 and 16), they cooperate to define the air flow path 660 that directs the air flow around and down towards the bottom of the tub 650 to the water surface. As illustrated, the air flow path has a generally circular configuration. The shape and structure of the air flow path 660 provides the guidance for the air flow. In an embodiment, the roof 657 and/or floor 661 may have a slope to promote spiral or helical motion.

The air outlet flow tube 667 is centrally located and formed in the lower portion 653 of the tub 650. This arrangement allows air to exit out the top of the tub 650. In this embodiment, the air outlet flow tube 667 is not positioned below the air inlet flow tube 655. However, the tub 650 does provide spill-back protection due to the barrier 669 between the upper and lower portions 651, 653 of the tub 650. This arrangement may be similar to the spill-back design used on ResMed's H3i Humidifier disclosed in WO 2004/112873, incorporated herein by reference in its entirety.

Figure 23:
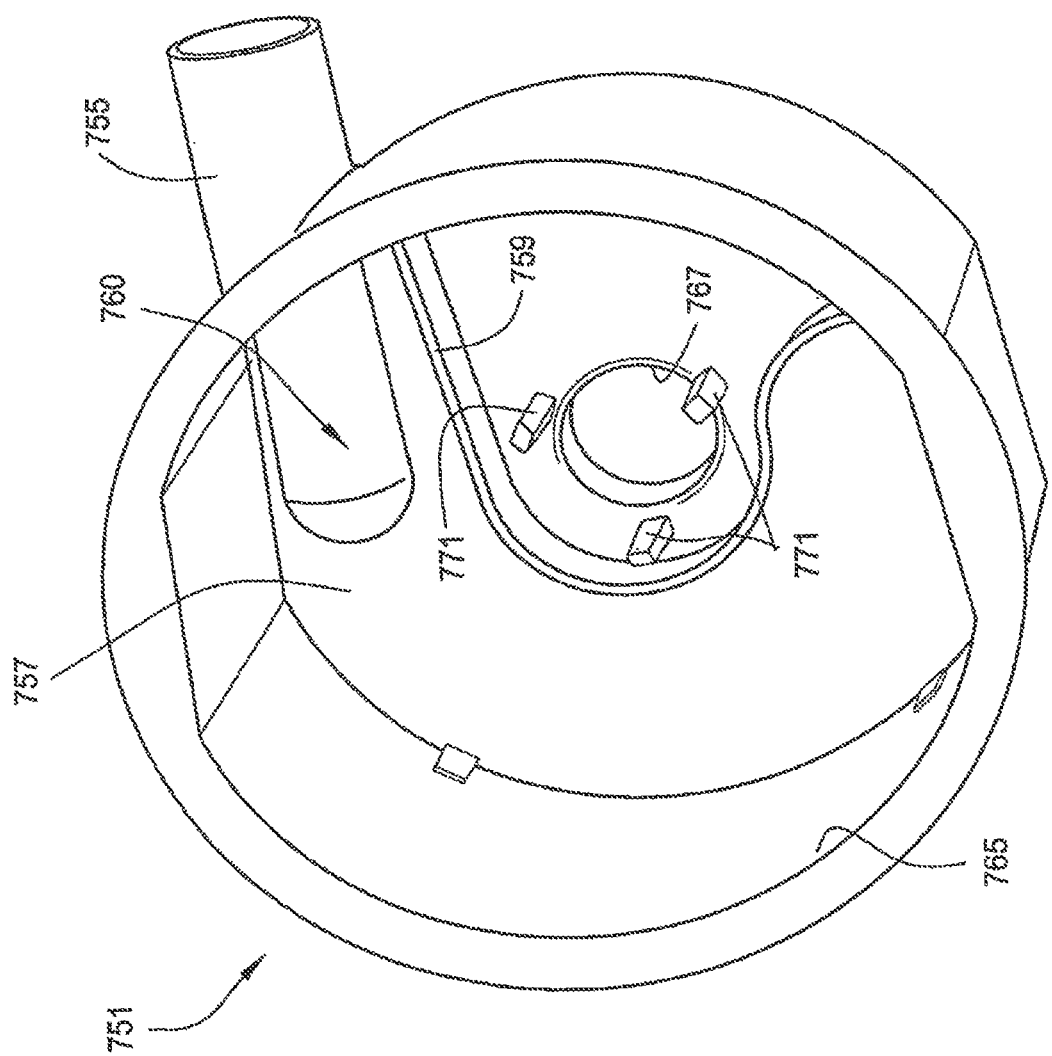
Figure 24:
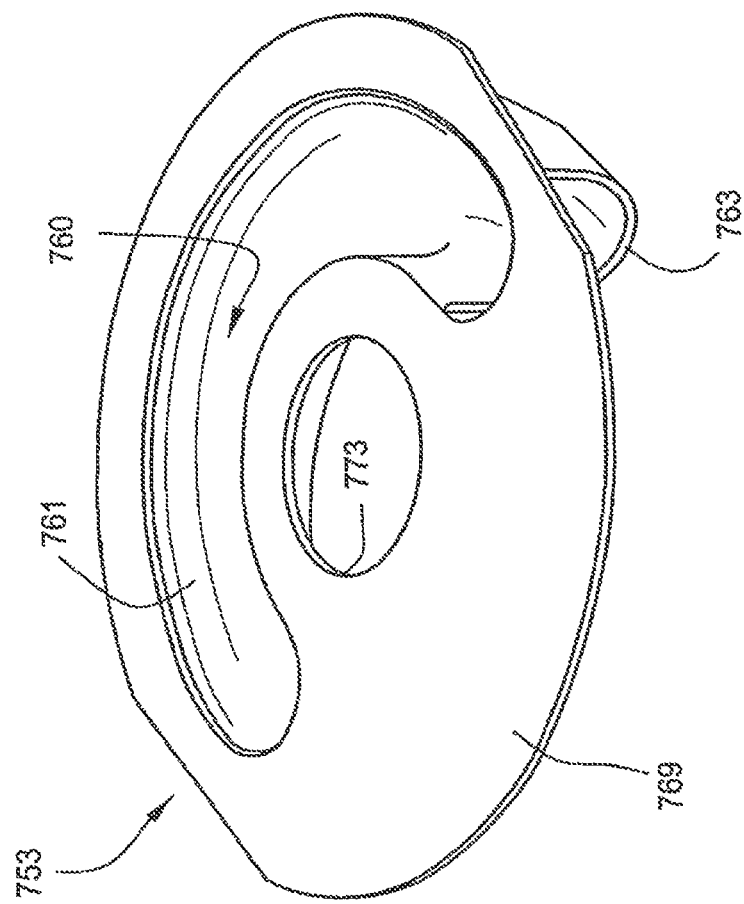
Figure 25:
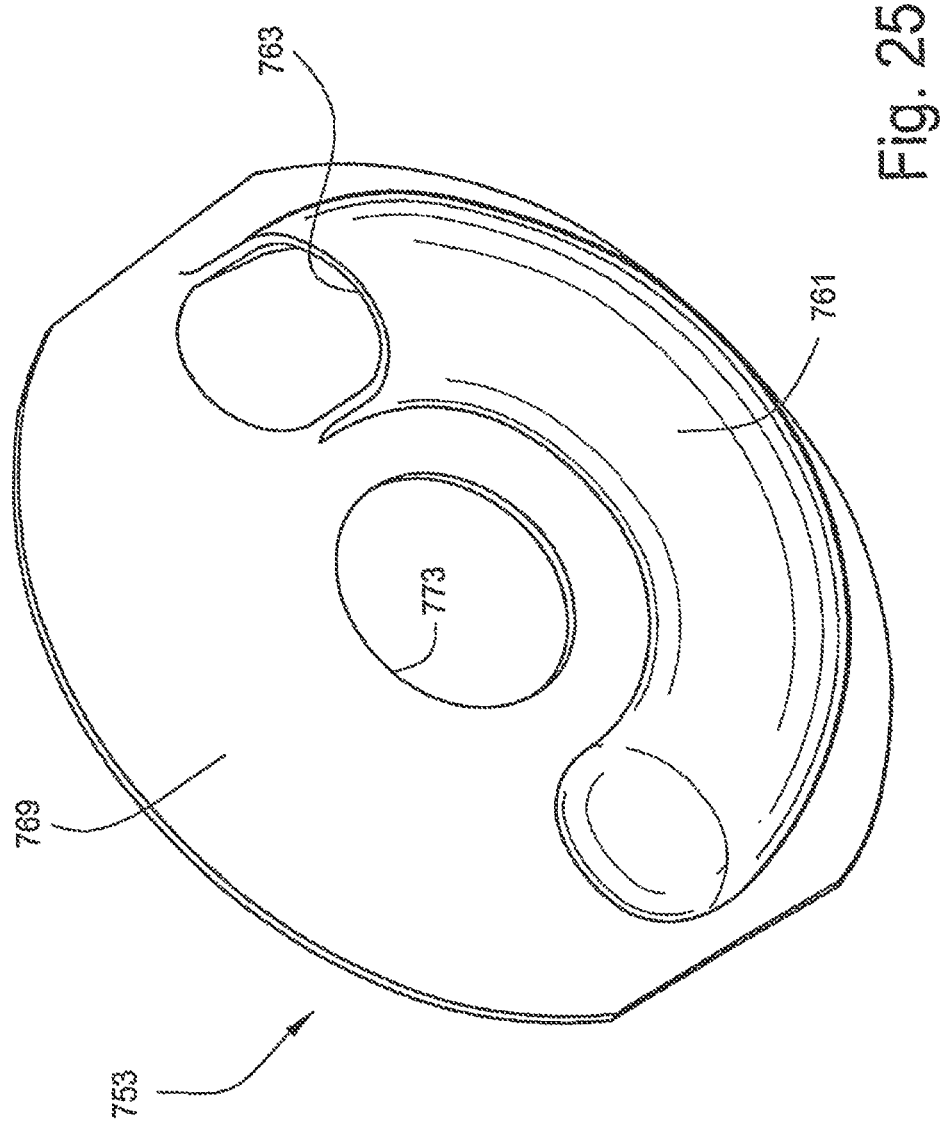

FIGS. 21-25 illustrate a humidifier tub 750 according to still another embodiment of the invention. As illustrated, the humidifier tub 750 is constructed of two separate components that are coupled to one another. Specifically, the humidifier tub 750 includes a tub portion 751 and a barrier portion 753 coupled to the tub portion 751. As best shown in FIG. 23, the tub portion 751 includes an air inlet flow tube 755 and a roof 757 and side sections 759 of an air flow path 760 that directs incoming air down and around within the tub 750. As best shown in FIGS. 24-25, the barrier portion 753 includes the floor or bottom section 761 of the air flow path 760 and provides a barrier 769 between the air flow path 760 and the bottom of the tub 750. An inlet opening 763 is provided that allows air to enter the chamber defined by the side wall 765 of the tub portion 751.

When the barrier portion 753 is coupled to the tub portion 751 (see FIG. 22), they cooperate to define the air flow path 760 that directs the air flow around and down towards the bottom of the tub 750 to the water surface. In the illustrated embodiment, the tub portion 751 includes locking members 771 that engage an aperture 773 provided in the barrier portion 753 with a snap-fit. However, the barrier portion 753 may be attached to the tub portion 751 in other suitable manners. As illustrated, the air flow path has a generally circular configuration. The shape and structure of the air flow path 760 provides the guidance for the air flow. In an embodiment, the roof 757 and/or floor 761 may have a slope to promote spiral or helical motion.

The air outlet flow tube 767 of the tub 750 is centrally located and formed in the tub portion 751 of the tub 750. This arrangement allows air to exit out the top of the tub 750.

1.6.1 Alternative Port Structure

As shown in FIGS. 2A and 2C, the humidifier tub has an outlet in the form of an outlet tube 54, 254 that extends upwards from an inset ledge. With this construction, an air delivery conduit (not shown) includes a fitting into which the conduit is inserted to establish fluid communication between the tub and the air delivery tube.

Figure 27:
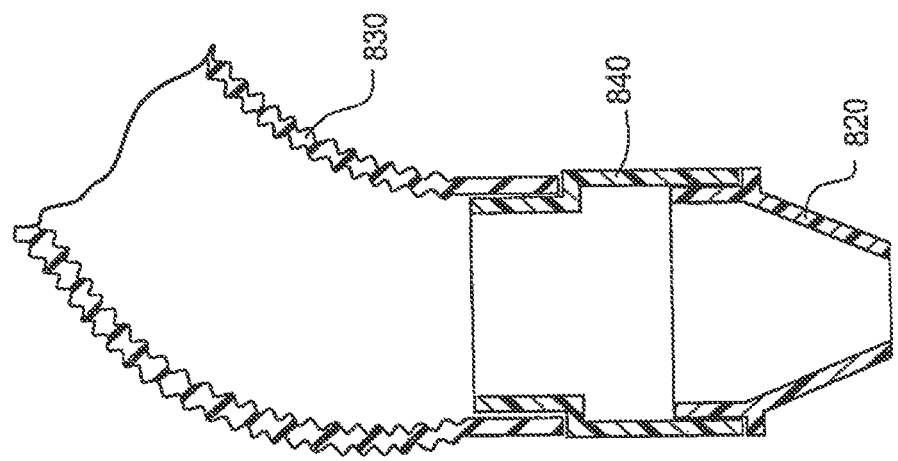
FIGS. 26-27 illustrate a humidifier tub and/or associated tubing/connector according to another embodiment of the invention.
Figure 26:
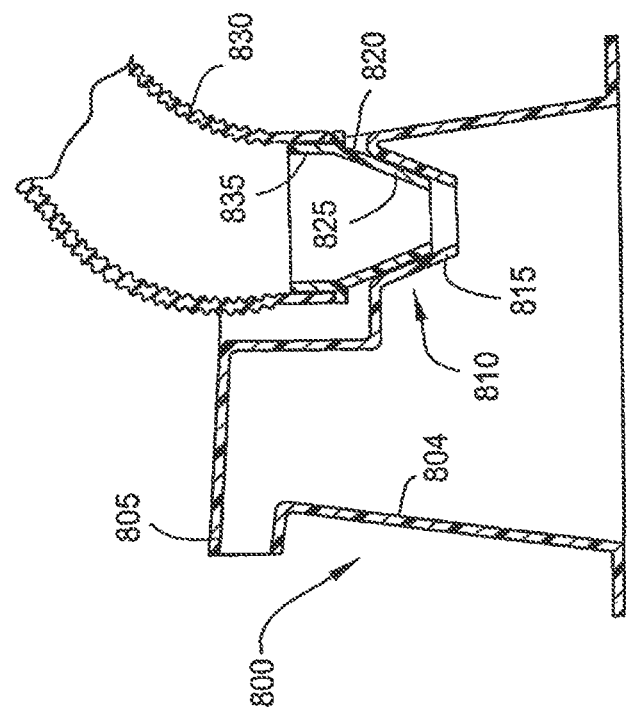

In an alternative as shown in FIG. 26, a humidifier tub 800 may include a main body 804 with an inlet conduit portion 805 like that shown in earlier embodiments and an outlet 810 which differs from the outlets shown in earlier embodiments. Outlet 810 includes a female fitting 815, preferably in the form of a conical section. Fitting 815 is compatible with a standard fitting 820 that has a lower portion 825 with a similarly shaped but smaller diameter conical fitting. Standard fitting 820 is inserted into or within the outlet fitting 815. An air delivery conduit 830 may be coupled to an upper portion 835 of the standard fitting 820. In use, the standard fitting 820 and the air delivery conduit 830 are preferably attached to and detached from the tub outlet 810 as one unit, which is easier for the patient or clinician since the mating of the two conical surfaces is generally self locating and takes less effort than standard connections where the user may struggle to attach the rubber fitting of air delivery conduit to the humidifier outlet, which connection may involve strong frictional forces. This arrangement also facilitates the use of an antibacterial filter 840 (FIG. 27) that has one end coupled to the standard fitting and another end coupled to the air delivery tube.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A humidifier tub with a chamber configured to contain a body of water and humidify a pressurized flow of respiratory gas, the humidifier tub comprising:
   a first side and a second side opposing the first side, the first side having an air inlet opening configured to receive the pressurized flow of respiratory gas;
   an air outlet opening configured to discharge the pressurized flow of respiratory gas with added humidity;
   an inlet passage extending from the air inlet opening toward the second side so that the pressurized flow of respiratory gas travels through the inlet passage in a first direction;
   a guidance structure located between the first and second sides and positioned so that a traveling direction of the pressurized flow of respiratory gas changes from the first direction to a second direction upon the pressurized flow of respiratory gas engaging the guidance structure;
   a lid forming a top side of the chamber, the guidance structure extending downward from the lid; and
   a heat conducting base plate located on a bottom side of the chamber,
   wherein the first direction is a lateral direction and the second direction is a downward direction.

2. The humidifier tub of claim 1, wherein the first and second directions are orthogonal to each other.

3. The humidifier tub of claim 1, further comprising an outlet passage extending into the chamber from the air outlet opening.

4. The humidifier tub of claim 1, wherein the guidance structure comprises a curved wall.

5. The humidifier tub of claim 1, wherein the guidance structure extends from an upper surface of the lid.

6. The humidifier tub of claim 1, wherein the inlet passage is integrally formed with an upper surface of the lid so that an upper surface of the inlet passage forms part of the lid.

7. The humidifier tub of claim 1, wherein the air outlet opening is not below the air inlet opening.

8. The humidifier tub of claim 1, wherein a bottom of the guidance structure is below the air outlet.

9. The humidifier tub of claim 1, wherein the guidance structure is located at an end of the inlet passage.

10. The humidifier tub of claim 1, further comprising an outlet passage extending into the chamber from the air outlet opening,
    wherein the first and second directions are orthogonal to each other,
    wherein the guidance structure comprises a curved wall,
    wherein the guidance structure extends from an upper surface of the lid,
    wherein the inlet passage is integrally formed with the upper surface of the lid so that an upper surface of the inlet passage forms part of the lid, and
    wherein the air outlet opening is not below the air inlet opening.

11. A respiratory device comprising:
    a flow generator configured to pressurize a flow of respiratory gas;
    the humidifier tub of claim 1; and
    a humidifier base configured to receive the humidifier tub.

12. The respiratory device of claim 11, further comprising a housing configured to support both the flow generator and the humidifier base.

13. The respiratory device of claim 12, wherein the humidifier base comprises a heater plate configured to engage the base plate of the humidifier tub upon the humidifier tub being received by the humidifier base.

14. A humidifier tub with a chamber configured to contain a body of water and humidify a pressurized flow of respiratory gas, the humidifier tub comprising:
    a first side and a second side opposite the first side, the first side having an air inlet opening configured to receive the pressurized flow of respiratory gas;
    an air outlet opening configured to discharge the pressurized flow of respiratory gas with added humidity;
    a guidance structure configured to direct the pressurized flow of respiratory gas through the chamber, the guidance structure comprising:
       a first portion configured to direct the respiratory gas in a first direction from the air inlet opening toward the second side of the humidifier tub; and
       a second portion located between the first and second sides of the humidifier tub and positioned so that a traveling direction of the pressurized flow of respiratory gas changes from the first direction to a second direction upon the pressurized flow of respiratory gas engaging the second portion of the guidance structure;
    a lid forming a top side of the chamber, the second portion of the guidance structure extending downward from the lid; and
    a heat conducting base plate located on a bottom side of the chamber,
    wherein the first direction is a generally horizontal direction and the second direction is a downward direction.

15. The humidifier tub of claim 14, wherein the first and second directions are orthogonal to each other.

16. The humidifier tub of claim 15, wherein the second portion of the guidance structure extends downward from an upper surface of the lid.

17. The humidifier tub of claim 15, wherein the first portion of the guidance structure is in the form of a laterally extending air flow passage that extends from the air inlet opening into the chamber.

18. The humidifier tub of claim 15, wherein the first direction is a generally horizontal direction and the second direction is a downward direction.

19. The humidifier tub of claim 15, further comprising an outlet passage extending into the chamber from the air outlet opening.

20. The humidifier tub of claim 15, wherein the second portion of the guidance structure comprises a curved wall.

21. The humidifier tub of claim 15, wherein the guidance structure extends from an upper surface of the lid.

22. The humidifier tub of claim 15, wherein the first portion of the guidance structure is integrally formed with an upper surface of the lid so that an upper surface of the first portion of the guidance structure forms part of the lid.

23. The humidifier tub of claim 15, wherein the air outlet opening is not below the air inlet opening.

24. The humidifier tub of claim 15, further comprising an outlet passage extending into the chamber from the air outlet opening,
   wherein the first and second directions are orthogonal to each other,
   wherein the second portion of the guidance structure extends downward from an upper surface of the lid,
   wherein the first portion of the guidance structure is in the form of a laterally extending air flow passage that extends from the air inlet opening into the chamber,
   wherein the second portion of the guidance structure comprises a curved wall,
   wherein the guidance structure extends from an upper surface of the lid,
   wherein the first portion of the guidance structure is integrally formed with an upper surface of the lid so that an upper surface of the first portion of the guidance structure forms part of the lid, and
   wherein the air outlet opening is not below the air inlet opening.

25. A respiratory device comprising:
   a flow generator configured to pressurize a flow of respiratory gas;
   the humidifier tub of claim 15; and
   a humidifier base configured to receive the humidifier tub.

26. The respiratory device of claim 25, further comprising a housing configured to support both the flow generator and the humidifier base.

27. The respiratory device of claim 26, wherein the humidifier base comprises a heater plate configured to engage the base plate of the humidifier tub upon the humidifier tub being received by the humidifier base.

\* \* \* \* \*